(12) United States Patent
Ilmén et al.

(10) Patent No.: US 6,326,477 B1
(45) Date of Patent: Dec. 4, 2001

(54) PROCESS FOR MODIFYING GLUCOSE REPRESSION

(75) Inventors: Marja Ilmén, Helsinki; Hans Söderlund, Espoo; Merja Penttilä, Helsinki, all of (FI)

(73) Assignee: Valtion Teknillinen Tutkimuskeskus, Espoo (FI)

( * ) Notice: Subject to any disclaimer, the term of this patent is extended or adjusted under 35 U.S.C. 154(b) by 0 days.

(21) Appl. No.: 09/029,755
(22) PCT Filed: Aug. 30, 1996
(86) PCT No.: PCT/FI96/00463
§ 371 Date: Mar. 2, 1998
§ 102(e) Date: Mar. 2, 1998
(87) PCT Pub. No.: WO97/09438
PCT Pub. Date: Mar. 13, 1997

(30) Foreign Application Priority Data

Sep. 1, 1995 (FI) .................................................. 954123

(51) Int. Cl.⁷ .................................................. C07H 21/02
(52) U.S. Cl. ............... 536/23.1; 536/23.1; 536/23.7; 536/24.32; 536/23.2; 530/350; 530/324; 530/300; 435/69.1; 435/252.3; 435/320.1; 435/6; 435/172.3; 435/69.8; 435/254.11; 435/7.1
(58) Field of Search .................... 435/69.1, 252.3, 435/320.1, 6, 172.3, 254.11, 69.8, 7.1; 536/23.1, 23.7, 24.32, 23.2; 530/324, 300, 350

(56) References Cited

U.S. PATENT DOCUMENTS

6,004,785 * 6/1995 Berka et al. ..................... 435/172.3

FOREIGN PATENT DOCUMENTS

WO 94/13820   6/1994 (WO) .

OTHER PUBLICATIONS

Takashima et al. Alignment: Accession No. D63514, Direct Submission. Aug. 14, 1995.*
Mathieu et al. (1994) The EMBO Journal. vol. 13, No. 17, pp. 4022–4027, 1994.*
Dowzer et al. (1991) Molecular and Cellular Biology. vol. 11, pp. 5701–5709, 1991.*

Celia E.A. Dowzer & Joan M. Kelly, "Molecular and Cellular Biology", Nov. 1991, pp. 5701–5709.

Martine Mathieu & Beatrice Felenbok, "The EMBO Journal", 1994, vol. 13 No. 17 pp. 4022–4027.

Aaron Klug & John W.R. Schwabe, "Zinc fingers", vol. 9, May 1995, pp. 597–604.

(Abstract) S. Takashima et al., "Cloning of a Gene Encoding a Putative Carbon Catabolite Repressor from *Trichoderma Reesei*", The University of Tokyo Department of Biotechnology (1995).

(Abstract) M. Ilmen et al., "The Glucose Repressor Gene Crel of Trichoderma—Isolation and Expression of a Full–Length and a Truncated Mutant Form", Molecular & General Genetics, 1996.

(Abstract) M.L. Waterman et al., "A Single Domain of the Estrogen Receptor Confers DNA Binding and Transcriptional Activation of the Rat Prolactin Gene", Molendocrinol 2 (1). 1988.

(Abstract) Christopher Bailey, "Carbon Catabolite Repression in *Aspergillus Nidulans* ", Eur. J. Biochem (1975), 51(2), 573–7.

* cited by examiner

Primary Examiner—Karen Cochrane Carlson
Assistant Examiner—Hope Robinson
(74) Attorney, Agent, or Firm—Crowell & Moring LLP

(57) ABSTRACT

The present invention relates to recombinant-DNA-technology, and particularly to genes involved in the control of basic metabolic processes in fungi. The invention specifically provides a mutated form of the native glucose repressor gene cre of filamentous fungi, wherein the mutation is situated in the C-terminal domain, the N-terminal first zinc finger being intact and the C-terminal region including the second zinc finger being mutated so that the viability of a strain carrying said mutated gene is maintained and the glucose repression is relieved.

19 Claims, 10 Drawing Sheets

| | | | |
|---|---|---|---|
| T.r. | Rut-C30 | MQRAQSAVDFSNLLNPTSAAGQDS------GAMSTAAVTV | 34 |
| T.r. | VTT-D-80133 | MQRAQSAVDFSNLLNPTSAAGQDS------GAMSTAAVTV | 34 |
| T.r. | QM9414 | MQRAQSAVDFSNLLNPTSAAGQDS------GAMSTAAVTV | 34 |
| T.h. | T3 | MQRAQSAVDFSNLLNPTSAAGQDSDAEQGSGAMSTAAVTV | 40 |
| | | ************************      *********** | |
| T.r. | Rut-C30 | IKPNGPIPGTQSTETANELPRPYKCPLCDKAFHRLEHQTR | 74 |
| T.r. | VTT-D-80133 | IKPNGPIPGTQSIETANELPRPYKCPLCDKAFHRLEHQTR | 74 |
| T.r. | QM9414 | IKPNGPIPGTQSTETANELPRPYKCPLCDKAFHRLEHQTR | 74 |
| T.h. | T3 | IKPNGPIPGAQSTEAANELPRPYKCPLCEKAFHRLEHQTR | 80 |
| | | ********* ** *** ********** *********** | |
| T.r. | Rut-C30 | HIRTHTGEKPHACTSITCFFF | 95 |
| T.r. | VTT-D-80133 | HIRTHTGEKPHACQFPGCSKKFSRSDELTRHSRIHSNPNS | 114 |
| T.r. | QM9414 | HIRTHTGEKPHACQFPGCSKKFSRSDELTRHSRIHSNPNS | 114 |
| T.h. | T3 | HIRTHTGEKPHACQFPGCSKKFSRSDELTRHSRIHSNPNS | 120 |
| | | ************* .  *   . *                | |
| T.r. | VTT-D-80133 | RRGNKGQQQHQ--LHHQGMPHPMHVDGLMHPPAAPKAIRS | 152 |
| T.r. | QM9414 | RRGNKGQQQHQ--LHHQGMPHPMHVDGLMHPPAAPKAIRS | 152 |
| T.h. | T3 | RRGNKGQQQHQQHQQHLHHQGLPHHMHVDGMM-PPPVPKAIRS | 159 |
| | | ***********  ***** **.* *.   ** ******* | |
| T.r. | VTT-D-80133 | APPSTLVSPNVSPPHSYSSFVMPHGPISHYGRGNDITMLA | 192 |
| T.r. | QM9414 | APPSTLVSPNVSPPHSYSSFVMPHGPISHYGRGNDITMLA | 192 |
| T.h. | T3 | APTSTLVSPNVSPPHSYSSFVMPQTPMAHYNRGNDITMLA | 199 |
| | |  ***************** . * .******* | |

Fig. 1A

```
T.r. VTT-D-80133    KAANQIERETLSGGPSNHNSRHHPYFGQGVPGSRGHP-SL  231
T.r. QM9414         KAANQIERETLSGGPSNHNSRHHPYFGQGVPGSRGHP-SL  231
T.h. T3             KAANQIERETLSGGPSNHNSRHHPYFGQGLPNSRGHPPSL  239
                    ************************.*.*.******.**

T.r. VTT-D-80133    SSYHMARAHSNDEDDHYGSLRHAKRSRPNSPNSTAPSSP  271
T.r. QM9414         SSYHMARAHSNDEDDHYGSLRHAKRSRPNSPNSTAPSSP  271
T.h. T3             SSYHMARSHSNDDDDHY-SSMRHAKRSRPNSPNSTAPSSP 278
                    *******.****..** .* .*****************

T.r. VTT-D-80133    TFSHDSLSPTPDHTPIATPAHSPRLRPFSGYELPSLRNLS  311
T.r. QM9414         TFSHDSLSPTPDHTPIATPAHSPRLRPFSGYELPSLRNLS  311
T.h. T3             TFSHDSLSPTPDHTPIATPAHSPRLRPFSGYELPSLRNLS  318
                    ***************************************

T.r. VTT-D-80133    LQHNTTPALAPMEPHLDAPQFHPQLQANTTRSPGMSLTDI  351
T.r. QM9414         LQHNTTPALAPMEPHLDAPQFHPQLQANTTRSPGMSLTDI  351
T.h. T3             LQHNTTPALAPMEPHLDAPQFPPQLQANNNRSPGMSLTDI  358
                    ********************* *****..**********

T.r. VTT-D-80133    ISRPDGSQRKLPVPQVPKVAVQDLLSDGVFPNSGRSSTTG  391
T.r. QM9414         ISRPDGSQRKLPVPQVPKVAVQDLLSDGVFPNSGRSSTTG  391
T.h. T3             ISRPDGSHRKLPVPQVPKVAVQDLLSDGVFPNSGRSSTAG  398
                    *******.******************************.*

T.r. VTT-D-80133    SLAGGDLMDRM  402
T.r. QM9414         SLAGGDLMDRM  402
T.h. T3             SLAGGDLMDRM  409
                    ***********
```

Fig. 1B

SEQUENCE LISTING

<160> NUMBER OF SEQ ID NOS: 21

<210> SEQ ID NO 1
<211> LENGTH: 2690
<212> TYPE: DNA
<213> ORGANISM: Trichoderma harzianum T3
<220> FEATURE:
<221> NAME/KEY: CDS
<222> LOCATION: (801)..(2027)

<400> SEQUENCE: 1

```
ccgagctggc atcggccatc tcactgagcc ctgtactagg tatctgaccc aagcgcacac      60
cccgccatcg caccccccct ccttgtggtc cccttcgccc cagctggggc tcccactgag     120
ggcgagggct ggggctttga atgctggggc tggctggtac aaacattcga gagcagccaa     180 gtacccgta  cccctttcgt gccctggcta cgtgtcccgt ctgctcccct ccagcgcccc     240
gtcgcgccat ccagcccact ggactgtgcc gtgcagtgct gtgcaccccc aaaggcactg     300
cctaagccct gcgtgacgcc cctgatttag agccgcgtgt agcgaggtct agcatgtgct     360
tgcgttgatg cattgaggta cttgtccgca agtacctgac tccctcccag tcccatgtac     420
gaagtaccga cccgggcgag cccgcccttga ttaaagcgat tgcctccccc agtccctcc     480
```

-continued

```
ttctcccgaa ggaaaaaaaa aagtctccct cgatcaagca aaacaaaacc acaccatagc      540
cactcaccca atctaatatc gcatctcgat cttccaacta ccgacgacaa gagcctcttt      600
gaccttagaa ggcaagcaac atcagcgtca acaccagcta caagcagata attacacagc     660
ggtcctgcac agcggtcctc cccactacaa ggacaacggc atataaccac tccaccagcg     720
gataatctct tgccaaccca cacgctcgct tctctggccg tctagtcaac gtttactcgc     780
tttggctgcc gctcgatcac atg caa cga gct cag tct gcc gtg gat ttt tcc    833
                      Met Gln Arg Ala Gln Ser Ala Val Asp Phe Ser
                       1               5                  10 aat cta ctt aat cca act tcg gca gca gga cag gac agc gac gcc gag      881
Asn Leu Leu Asn Pro Thr Ser Ala Ala Gly Gln Asp Ser Asp Ala Glu
         15                  20                  25 caa ggc agc gga gcc atg tct acc gct gcg gtt acc gtc atc aag ccc      929
Gln Gly Ser Gly Ala Met Ser Thr Ala Ala Val Thr Val Ile Lys Pro
     30                  35                  40 aat ggg cct atc cca gga gca cag tca acg gag gct gcc aac gag ctt      977
Asn Gly Pro Ile Pro Gly Ala Gln Ser Thr Glu Ala Ala Asn Glu Leu
 45                  50                  55 cct cgt ccc tac aag tgc cct ctt tgt gaa aag gcc ttc cac cgt ctg     1025
Pro Arg Pro Tyr Lys Cys Pro Leu Cys Glu Lys Ala Phe His Arg Leu
60                  65                  70                  75 gag cac cag acc agg cac atc cgc act cac acg ggc gag aag ccc cat     1073
Glu His Gln Thr Arg His Ile Arg Thr His Thr Gly Glu Lys Pro His
                 80                  85                  90 gcc tgc cag ttc cct ggc tgc agc aag aag ttc tct cgt tcc gat gag     1121
Ala Cys Gln Phe Pro Gly Cys Ser Lys Lys Phe Ser Arg Ser Asp Glu
             95                 100                 105 ttg acc agg cac tcg agg ata cac agc aac ccc aac tcc agg cgc ggc     1169
Leu Thr Arg His Ser Arg Ile His Ser Asn Pro Asn Ser Arg Arg Gly
        110                 115                 120 aac aag ggc cag cag cag cac caa cag cac ctt cac cac caa ggc ctt     1217
Asn Lys Gly Gln Gln Gln His Gln Gln His Leu His His Gln Gly Leu
    125                 130                 135 cct cac cac atg cac gtc gat ggc atg atg ccc cct ccg gtg cca aag     1265
Pro His His Met His Val Asp Gly Met Met Pro Pro Pro Val Pro Lys
140                 145                 150                 155 gcc atc cgc tct gct ccc acc tcg act ctg gtc tcg cct aac gtc tcg     1313
Ala Ile Arg Ser Ala Pro Thr Ser Thr Leu Val Ser Pro Asn Val Ser
                160                 165                 170 cct ccc cac tct tac tcc tcg ttt gtc atg ccc cag acc ccc atg gct     1361
Pro Pro His Ser Tyr Ser Ser Phe Val Met Pro Gln Thr Pro Met Ala
            175                 180                 185 cac tac aac cgt ggc aac gat atc aca atg ctg gca aag gct gca aac     1409
His Tyr Asn Arg Gly Asn Asp Ile Thr Met Leu Ala Lys Ala Ala Asn
        190                 195                 200 cag atc gag cgg gaa act ctc tct ggc ggc ccg tct aac cac aac tca     1457
Gln Ile Glu Arg Glu Thr Leu Ser Gly Gly Pro Ser Asn His Asn Ser
    205                 210                 215 agg cat cat ccc tac ttc ggc cag ggc ttg ccg aac tct cga ggc cac     1505
Arg His His Pro Tyr Phe Gly Gln Gly Leu Pro Asn Ser Arg Gly His
220                 225                 230                 235 ccg cct tcc ctt tcc tcg tac cac atg gcg aga tct cac tcc aat gac     1553
Pro Pro Ser Leu Ser Ser Tyr His Met Ala Arg Ser His Ser Asn Asp
                240                 245                 250 gat gat gat cat tac agc agc atg agg cac gcc aag agg tcg agg cct     1601
Asp Asp Asp His Tyr Ser Ser Met Arg His Ala Lys Arg Ser Arg Pro
            255                 260                 265 aac tcg ccc aac tcc acg gct ccc tct tct ccc acc ttt tcc cac gac     1649
```

-continued

```
Asn Ser Pro Asn Ser Thr Ala Pro Ser Ser Pro Thr Phe Ser His Asp
            270                 275                 280 tct ctg tct ccc acc ccg gat cac act ccc atc gca act ccc gct cac      1697
Ser Leu Ser Pro Thr Pro Asp His Thr Pro Ile Ala Thr Pro Ala His
285                 290                 295 tcc cct cga ctc cgc ccc ttt tcg ggc tat gag ctg ccg agt ctg aga      1745
Ser Pro Arg Leu Arg Pro Phe Ser Gly Tyr Glu Leu Pro Ser Leu Arg
300                 305                 310                 315 aac ctg tct ctg cag cac aac acg act ccg gcg ctg gcc ccc atg gag      1793
Asn Leu Ser Leu Gln His Asn Thr Thr Pro Ala Leu Ala Pro Met Glu
                320                 325                 330 ccc cac ctg gat gct ccc cag ttc ccc cct cag ctg cag gca aac aac      1841
Pro His Leu Asp Ala Pro Gln Phe Pro Pro Gln Leu Gln Ala Asn Asn
            335                 340                 345 aac cgc agc ccc ggc atg tcg ctt acc gac atc atc agc cgc ccc gac      1889
Asn Arg Ser Pro Gly Met Ser Leu Thr Asp Ile Ile Ser Arg Pro Asp
        350                 355                 360 ggg agc cac agg aag ctc cct gtt cct cag gtt ccc aag gtg gcg gtg      1937
Gly Ser His Arg Lys Leu Pro Val Pro Gln Val Pro Lys Val Ala Val
365                 370                 375 cag gac ctc ctc tca gac ggt gta ttc cct aac agc ggc aga agt tca      1985
Gln Asp Leu Leu Ser Asp Gly Val Phe Pro Asn Ser Gly Arg Ser Ser
380                 385                 390                 395 act gca ggc agt ctt gca ggt ggc gac ctc atg gat cgg atg              2027
Thr Ala Gly Ser Leu Ala Gly Gly Asp Leu Met Asp Arg Met
                400                 405 tagagaatcc cttactttgg cgcctcgaat gacttgatga ctttgggcta tagaaggata   2087
gaaagagacg gcgtttatgg catggaaatg aaatggaaat ggaaagagtc gtccctcgaa   2147
ggacttgaca cggctatttt tttcttccct tttttgttt tctttacttg attttttttt   2207
cattgcaggg catggaatcc tacacaagat ggatggccaa aggaaatata gacatcacca   2267
cttccccaac ggattactgt tgactactac cttttttttt ctgtttcttc tcttctcttg   2327
tttctggttg tttctataca gtggaagatt tattattgga ttcaactgaa agttggccca   2387
aaaaatcgaa aaagacatga ttatttttac acactcacgc gctccaatct ttcatcaatt   2447
tctgtacaac caaatatttt tcttttttact tgttgtttct tggtatcttt gcatcccaca   2507
tgccgctaga aagcccgtct ccggcatttg gcatctgagg gcttcggcaa cggcatgggc   2567
tggcatttga ctggggaata ccaaaacacg tttggtgtta caaatatagg ggaaacctca   2627
tgcactatgg gggaggcggc agcgctattc agggtggac aggtaatgga gggggattg     2687 aag                                                                 2690

<210> SEQ ID NO 2
<211> LENGTH: 409
<212> TYPE: PRT
<213> ORGANISM: Trichoderma harzianum T3

<400> SEQUENCE: 2

Met Gln Arg Ala Gln Ser Ala Val Asp Phe Ser Asn Leu Leu Asn Pro
1               5                   10                  15

Thr Ser Ala Ala Gly Gln Asp Ser Asp Ala Glu Gln Gly Ser Gly Ala
            20                  25                  30

Met Ser Thr Ala Ala Val Thr Val Ile Lys Pro Asn Gly Pro Ile Pro
        35                  40                  45

Gly Ala Gln Ser Thr Glu Ala Ala Asn Glu Leu Pro Arg Pro Tyr Lys
    50                  55                  60
```

```
Cys Pro Leu Cys Glu Lys Ala Phe His Arg Leu Glu His Gln Thr Arg
 65                  70                  75                  80

His Ile Arg Thr His Thr Gly Glu Lys Pro His Ala Cys Gln Phe Pro
                 85                  90                  95

Gly Cys Ser Lys Lys Phe Ser Arg Ser Asp Glu Leu Thr Arg His Ser
            100                 105                 110

Arg Ile His Ser Asn Pro Asn Ser Arg Arg Gly Asn Lys Gly Gln Gln
        115                 120                 125

Gln His Gln Gln His Leu His Gln Gly Leu Pro His His Met His
130                 135                 140

Val Asp Gly Met Met Pro Pro Val Pro Lys Ala Ile Arg Ser Ala
145                 150                 155                 160

Pro Thr Ser Thr Leu Val Ser Pro Asn Val Ser Pro Pro His Ser Tyr
                165                 170                 175

Ser Ser Phe Val Met Pro Gln Thr Pro Met Ala His Tyr Asn Arg Gly
            180                 185                 190

Asn Asp Ile Thr Met Leu Ala Lys Ala Ala Asn Gln Ile Glu Arg Glu
        195                 200                 205

Thr Leu Ser Gly Gly Pro Ser Asn His Asn Ser Arg His His Pro Tyr
210                 215                 220

Phe Gly Gln Gly Leu Pro Asn Ser Arg Gly His Pro Ser Leu Ser
225                 230                 235                 240

Ser Tyr His Met Ala Arg Ser His Ser Asn Asp Asp Asp His Tyr
                245                 250                 255

Ser Ser Met Arg His Ala Lys Arg Ser Arg Pro Asn Ser Pro Asn Ser
            260                 265                 270

Thr Ala Pro Ser Ser Pro Thr Phe Ser His Asp Ser Leu Ser Pro Thr
        275                 280                 285

Pro Asp His Thr Pro Ile Ala Thr Pro Ala His Ser Pro Arg Leu Arg
290                 295                 300

Pro Phe Ser Gly Tyr Glu Leu Pro Ser Leu Arg Asn Leu Ser Leu Gln
305                 310                 315                 320

His Asn Thr Thr Pro Ala Leu Ala Pro Met Glu Pro His Leu Asp Ala
                325                 330                 335

Pro Gln Phe Pro Pro Gln Leu Gln Ala Asn Asn Arg Ser Pro Gly
            340                 345                 350

Met Ser Leu Thr Asp Ile Ile Ser Arg Pro Asp Gly Ser His Arg Lys
        355                 360                 365

Leu Pro Val Pro Gln Val Pro Lys Val Ala Val Gln Asp Leu Leu Ser
370                 375                 380

Asp Gly Val Phe Pro Asn Ser Gly Arg Ser Ser Thr Ala Gly Ser Leu
385                 390                 395                 400

Ala Gly Gly Asp Leu Met Asp Arg Met
                405
```

<210> SEQ ID NO 3
<211> LENGTH: 2877
<212> TYPE: DNA
<213> ORGANISM: Trichoderma reesei VTT-D-80133
<220> FEATURE:
<221> NAME/KEY: unsure
<222> LOCATION: (2623)
<223> OTHER INFORMATION: can be a, c, g or t

<400> SEQUENCE: 3
ccatctgctg gggtgcaagg ctgctaggca atacttggca ctatctgctt ggggcacgcc    60

-continued

```
ccgccatctg cacaccccac ccctcgcgc ccactccac tggctccttc cctgtggccc      120 tgcccttcg ccccagctgg ggctcccact gcaactgagg ccaagggctg gggggctct      180 gaaatgctgg ggcgcgaggt acaaccgtct gagagccgac aagtaccccg tgcccctt       240 ctggccgtct ctgagccctg cgacgtgtc ccgtccctct gccccctcg tccttccagc       300 gccccatcgc gccatcgagc cactggacgg tggcatgcag cgctgttgca ccccaaatg      360 tcgctgccta agccctgcgt gacgcccctg atttaccgcc ccgtgtagcg accgcagcat     420
gtgcttcgcg gtggtgcggt cggggtactt gcccacaagt accgcctcc caggtacagc     480 acggtacgca caccacgtac tcccgcactt gccctccctg gcgcccatgc tacgaatcga    540
agtaccgacc cggccgagcc cgcccttatt aaagcgattg cctccccc gtcccctcct      600 tctcccggag gaaaaaaaaa aaaagttcg ttctccctcg atgaacgaag aaaaaacaac     660
caccagaacc acactcactc acacccctc acatcgcatc tcgatcctgc aactaccgac     720
gacaagagcc tcgctcattt gaccagagaa gaatcgttat caccagcgct acccaccgcc    780
cagcagatat ctgtatagat cagcagtctc tcctccccgc aaacgaggac caccgcatac    840
tagcagagcc tgctcccgcc aaaaacccac actcgcttct ctgggctctc ttgtaaccaa    900
agaccaagtt gtcgcctcaa cgtcgcgtac ttgcttttg actgccgctc gatcacatgc    960
aacgagcaca gtctgccgtg gatttttcca acctcctgaa tccaacgtcg gcagcaggac   1020
aggacagcgg cgccatgtct accgccgcgc tcaccgtcat caagcccaat gggcccattc   1080
caggaacaca gtcgatcgag actgccaacg agctgcctcg tccctacaag tgccctcttt   1140
gcgacaaggc tttccaccgc ctggagcacc agaccaggca cattcgcacc cacacgggcg   1200
agaagcccca tgcctgccag ttccctggct gcagcaagaa gttctcccgc tccgatgagc   1260
tgacgaggca ctcgaggata cacagcaacc ccaactcaag gcgcggcaac aagggccagc   1320
agcagcacca gcttcaccac cagggcatgc ctcacccat gcacgtcgat ggcttgatgc    1380
accctcccgc cgcgccaaag gccatccgct ctgcgccccc ttcgaccctc gtctctccca   1440
acgtctcgcc tccgcactcc tactcgtcct ttgtcatgcc tcacggtccc atttctcact   1500
atggccgtgg caacgacatt acgatgcttg ccaaggcggc aaatcagatt gagcgcgaga   1560
cgctttctgg cgggccgtcc aaccacaact cgaggcacca cccttacttt ggccagggtg   1620 ttccggggttc tcgaggccac ccctcgcttt cttcgtacca catggcgaga gctcactcca   1680
acgacgagga tgaccactac catggcagct tgaggcacgc caagaggtca aggcccaact   1740
cgcccaactc tacggctcct tcttctccca ccttttcgca cgactctctg tcccccaccc   1800
cggatcacac tccatcgca actcccgctc actccccccg tctccgtccc ttttcgggct    1860
acgagctgcc gagtctgaga aacctgtccc tgcagcacaa tacgactccg gcgctggccc   1920
ccatggagcc tcacctggac gctccgcagt tccaccctca gctgcaggca acaccaccc    1980 gcagccccgg catgtcactt accgacatca ttagccgccc cgacggcagt cagaggaaac   2040
tgcctgtccc tcaggtcccc aagtggcgg ttcaggacct tctctccgac ggcgtcttcc    2100
ccaacagcgg cagaagttcc accacgggca gtcttgccgg tggcgacctc atggatcgga   2160
tgtagaatgt ccgtactca tggcgcgcat cgaatgactt acgactttgg gctatagatg     2220
gatagaaaga gttggcgtta atggtttgga aatggcaagg gaaatggata cggaaatgga    2280
aatggacaga gtcgtccccc gcaggacttg acacgggcta ttttggtttc tcttcttgt     2340 tccttttttc gtgtgctttt tttattcaat ttttttcttc ttgtacgctt ggatggaccc    2400
```

-continued

```
ctacacaata tggatggccc aggaaatata gacatcacca ctttcccaa cggactatta    2460 tctgctgttc cgtacagctt tggtcccatg ctttgttgtt tttgagccct ctacctggt    2520 acgactacag cggaggacta cttagattca gcggctgcct gttgtacttg caacgcaaaa    2580
ccaaaagagg ccagccaaaa gagaccatga tacaaagcat gcnctcccg cttagttttg    2640 atttatatgc acacagacta atatgcctgt tttttgtctc ctaagttgcg ctgctcgctg    2700
gtccgtcact tgcgttacac acatcgctag aaaaagctgg actcggcact tggcctctgc    2760
gaggttcggc accgcagcgg gatgggcagg ttcccttttcc ttttcccct ctgggggaat    2820 gaaccaaaac atgcctggtg ttacaaaata tggggaatcc ttatgcagtc tgggggg      2877
```

<210> SEQ ID NO 4
<211> LENGTH: 1946
<212> TYPE: DNA
<213> ORGANISM: Trichoderma reesei QM 9414
<220> FEATURE:
<221> NAME/KEY: CDS
<222> LOCATION: (289)..(1497)

<400> SEQUENCE: 4

```
ccacactcac tcacacaccc tcacatcgca tctcgatcct gcaactaccg acgacaagag    60
cctcgctcat ttgaccagag aagaatcgtt atcaccagcg ctaccaccg cccagcagat    120 atctgtatag atcagcagtc tctcctcccc gcaaacgagg accaccgcat actagcagag    180
cctgctcccg ccaaaaaccc cactcgcttt ctctgggctc tcttgtaacc aaagaccaag    240
ttgtcgcctc aacgtcgcgt acttgctttt tgactgccgc tcgatcac atg caa cga    297
                                                     Met Gln Arg
                                                      1 gca cag tct gcc gtg gat ttt tcc aac ctc ctg aat cca acg tcg gca    345
Ala Gln Ser Ala Val Asp Phe Ser Asn Leu Leu Asn Pro Thr Ser Ala
        5                  10                  15 gca gga cag gac agc ggc gcc atg tct acc gcc gcg gtc acc gtc atc    393
Ala Gly Gln Asp Ser Gly Ala Met Ser Thr Ala Ala Val Thr Val Ile
 20                  25                  30                  35 aag ccc aat ggg ccc att cca gga aca cag tcg acc gag act gcc aac    441
Lys Pro Asn Gly Pro Ile Pro Gly Thr Gln Ser Thr Glu Thr Ala Asn
                40                  45                  50 gag ctg cct cgt ccc tac aag tgc cct ctt tgc gac aag gct ttc cac    489
Glu Leu Pro Arg Pro Tyr Lys Cys Pro Leu Cys Asp Lys Ala Phe His
            55                  60                  65 cgc ctg gag cac cag acc agg cac att cgc acc cac acg ggc gag aag    537
Arg Leu Glu His Gln Thr Arg His Ile Arg Thr His Thr Gly Glu Lys
     70                  75                  80 ccc cat gcc tgc cag ttc cct ggc tgc agc aag aag ttc tcc cgc tcc    585
Pro His Ala Cys Gln Phe Pro Gly Cys Ser Lys Lys Phe Ser Arg Ser
 85                  90                  95 gat gag ctg acg agg cac tcg agg ata cac agc aac ccc aac tca agg    633
Asp Glu Leu Thr Arg His Ser Arg Ile His Ser Asn Pro Asn Ser Arg
100                 105                 110                 115 cgc ggc aac aag ggc cag cag cag cac cag ctt cac cac cag ggc atg    681
Arg Gly Asn Lys Gly Gln Gln Gln His Gln Leu His His Gln Gly Met
                120                 125                 130 cct cac ccc atg cac gtc gat ggc ttg atg cac cct ccc gcc gcg cca    729
Pro His Pro Met His Val Asp Gly Leu Met His Pro Pro Ala Ala Pro
            135                 140                 145 aag gcc atc cgc tct gcg ccc cct tcg acc ctc gtc tct ccc aac gtc    777
Lys Ala Ile Arg Ser Ala Pro Pro Ser Thr Leu Val Ser Pro Asn Val
    150                 155                 160
```

-continued

```
tcg cct ccg cac tcc tac tcg tcc ttt gtc atg cct cac ggt ccc att      825
Ser Pro Pro His Ser Tyr Ser Ser Phe Val Met Pro His Gly Pro Ile
    165                 170                 175 tct cac tat ggc cgt ggc aac gac att acg atg ctt gcc aag gcg gca      873
Ser His Tyr Gly Arg Gly Asn Asp Ile Thr Met Leu Ala Lys Ala Ala
180                 185                 190                 195 aat cag att gag cgc gag acg ctt tct ggc ggg ccg tcc aac cac aac      921
Asn Gln Ile Glu Arg Glu Thr Leu Ser Gly Gly Pro Ser Asn His Asn
                200                 205                 210 tcg agg cac cac cct tac ttt ggc cag ggt gtt ccg ggt tct cga ggc      969
Ser Arg His His Pro Tyr Phe Gly Gln Gly Val Pro Gly Ser Arg Gly
            215                 220                 225 cac ccc tcg ctt tct tcg tac cac atg gcg aga gct cac tcc aac gac     1017
His Pro Ser Leu Ser Ser Tyr His Met Ala Arg Ala His Ser Asn Asp
        230                 235                 240 gag gat gac cac tac cat ggc agc ttg agg cac gcc aag agg tca agg     1065
Glu Asp Asp His Tyr His Gly Ser Leu Arg His Ala Lys Arg Ser Arg
    245                 250                 255 ccc aac tcg ccc aac tct acg gct cct tct tct ccc acc ttt tcg cac     1113
Pro Asn Ser Pro Asn Ser Thr Ala Pro Ser Ser Pro Thr Phe Ser His
260                 265                 270                 275 gac tct ctg tcc ccc acc ccg gat cac act ccc atc gca act ccc gct     1161
Asp Ser Leu Ser Pro Thr Pro Asp His Thr Pro Ile Ala Thr Pro Ala
                280                 285                 290 cac tcc ccc cgt ctc cgt ccc ttt tcg ggc tac gag ctg ccg agt ctg     1209
His Ser Pro Arg Leu Arg Pro Phe Ser Gly Tyr Glu Leu Pro Ser Leu
            295                 300                 305 aga aac ctg tcc ctg cag cac aat acg act ccg gcg ctg gcc ccc atg     1257
Arg Asn Leu Ser Leu Gln His Asn Thr Thr Pro Ala Leu Ala Pro Met
        310                 315                 320 gag cct cac ctg gac gct ccg cag ttc cac cct cag ctg cag gca aac     1305
Glu Pro His Leu Asp Ala Pro Gln Phe His Pro Gln Leu Gln Ala Asn
    325                 330                 335 acc acc cgc agc ccc ggc atg tca ctt acc gac atc att agc cgc ccc     1353
Thr Thr Arg Ser Pro Gly Met Ser Leu Thr Asp Ile Ile Ser Arg Pro
340                 345                 350                 355 gac ggc agt cag agg aaa ctg cct gtc cct cag gtc ccc aag gtg gcg     1401
Asp Gly Ser Gln Arg Lys Leu Pro Val Pro Gln Val Pro Lys Val Ala
                360                 365                 370 gtt cag gac ctt ctc tcc gac ggc gtc ttc ccc aac agc ggc aga agt     1449
Val Gln Asp Leu Leu Ser Asp Gly Val Phe Pro Asn Ser Gly Arg Ser
            375                 380                 385 tcc acc acg ggc agt ctt gcc ggt ggc gac ctc atg gat cgg atg tag     1497
Ser Thr Thr Gly Ser Leu Ala Gly Gly Asp Leu Met Asp Arg Met
        390                 395                 400 aatgtccggt actcatggcg cgcatcgaat gacttacgac tttgggctat agatggatag   1557
aaagagttgg cgttaatggt ttggaaatgg caagggaaat ggatacggaa atggaaatgg   1617
acagagtcgt cccccgcagg acttgacacg ggctattttg gttttctcct tcttgttcct   1677
tttttcgtgt gctttttttta ttcaattttt ttcttcttgt acgcttggat ggaccoctac   1737 acaatatgga tggcccagga aatatagaca tcaccacttt ccccaacgga ctattatctg   1797
ctgttccgta cagcttttggt cccatgcttt gttgttttttg agcccttcta cctggtacga   1857
ctacagcgga ggactactta gattcagcgg ctgcctgttg tacttgcaac gcaaaaccaa   1917
aagaggccag ccaaaagaga ccatgatac                                    1946
```

<210> SEQ ID NO 5
<211> LENGTH: 402

```
<212> TYPE: PRT
<213> ORGANISM: Trichoderma reesei QM 9414

<400> SEQUENCE: 5

Met Gln Arg Ala Gln Ser Ala Val Asp Phe Ser Asn Leu Leu Asn Pro
 1               5                  10                  15

Thr Ser Ala Ala Gly Gln Asp Ser Gly Ala Met Ser Thr Ala Ala Val
             20                  25                  30

Thr Val Ile Lys Pro Asn Gly Pro Ile Pro Gly Thr Gln Ser Thr Glu
         35                  40                  45

Thr Ala Asn Glu Leu Pro Arg Pro Tyr Lys Cys Pro Leu Cys Asp Lys
     50                  55                  60

Ala Phe His Arg Leu Glu His Gln Thr Arg His Ile Arg Thr His Thr
 65                  70                  75                  80

Gly Glu Lys Pro His Ala Cys Gln Phe Pro Gly Cys Ser Lys Lys Phe
                 85                  90                  95

Ser Arg Ser Asp Glu Leu Thr Arg His Ser Arg Ile His Ser Asn Pro
            100                 105                 110

Asn Ser Arg Arg Gly Asn Lys Gly Gln Gln Gln His Gln Leu His His
            115                 120                 125

Gln Gly Met Pro His Pro Met His Val Asp Gly Leu Met His Pro Pro
130                 135                 140

Ala Ala Pro Lys Ala Ile Arg Ser Ala Pro Pro Ser Thr Leu Val Ser
145                 150                 155                 160

Pro Asn Val Ser Pro Pro His Ser Tyr Ser Ser Phe Val Met Pro His
                165                 170                 175

Gly Pro Ile Ser His Tyr Gly Arg Gly Asn Asp Ile Thr Met Leu Ala
            180                 185                 190

Lys Ala Ala Asn Gln Ile Glu Arg Glu Thr Leu Ser Gly Gly Pro Ser
            195                 200                 205

Asn His Asn Ser Arg His His Pro Tyr Phe Gly Gln Gly Val Pro Gly
210                 215                 220

Ser Arg Gly His Pro Ser Leu Ser Ser Tyr His Met Ala Arg Ala His
225                 230                 235                 240

Ser Asn Asp Glu Asp Asp His Tyr His Gly Ser Leu Arg His Ala Lys
                245                 250                 255

Arg Ser Arg Pro Asn Ser Pro Asn Ser Thr Ala Pro Ser Ser Pro Thr
            260                 265                 270

Phe Ser His Asp Ser Leu Ser Pro Thr Pro Asp His Thr Pro Ile Ala
            275                 280                 285

Thr Pro Ala His Ser Pro Arg Leu Arg Pro Phe Ser Gly Tyr Glu Leu
        290                 295                 300

Pro Ser Leu Arg Asn Leu Ser Leu Gln His Asn Thr Thr Pro Ala Leu
305                 310                 315                 320

Ala Pro Met Glu Pro His Leu Asp Ala Pro Gln Phe His Pro Gln Leu
                325                 330                 335

Gln Ala Asn Thr Thr Arg Ser Pro Gly Met Ser Leu Thr Asp Ile Ile
            340                 345                 350

Ser Arg Pro Asp Gly Ser Gln Arg Lys Leu Pro Val Pro Gln Val Pro
        355                 360                 365

Lys Val Ala Val Gln Asp Leu Leu Ser Asp Gly Val Phe Pro Asn Ser
    370                 375                 380

Gly Arg Ser Ser Thr Thr Gly Ser Leu Ala Gly Gly Asp Leu Met Asp
385                 390                 395                 400
```

Arg Met

<210> SEQ ID NO 6
<211> LENGTH: 1308
<212> TYPE: DNA
<213> ORGANISM: Trichoderma reesei RUT-C30
<220> FEATURE:
<221> NAME/KEY: CDS
<222> LOCATION: (316)..(603)

<400> SEQUENCE: 6

| | |
|---|---:|
| tgaacgaaga aaaaacaacc accagaacca cactcactca cacaccctca catcgcatct | 60 |
| cgatcctgca actaccgacg acaagagcct cgctcatttg accagagaag aatcgttatc | 120 |
| accagcgcta cccaccgccc agcagatatc tgtatagatc agcagtctct cctccccgca | 180 |
| aacgaggacc accgcatact agcagagcct gctcccgcca aaacccaca ctcgcttctc | 240 |
| tgggctctct tgtaaccaaa gaccaagttg tcgcctcaac gtcgcgtact tgcttttga | 300 |
| ctgccgctcg atcac atg caa cga gca cag tct gcc gtg gat ttt tcc aac | 351 |
|                   Met Gln Arg Ala Gln Ser Ala Val Asp Phe Ser Asn | |
|                   1          5              10 | |
| ctc ctg aat cca acg tcg gca gca gga cag gac agc ggc gcc atg tct | 399 |
| Leu Leu Asn Pro Thr Ser Ala Ala Gly Gln Asp Ser Gly Ala Met Ser | |
|         15              20              25 | |
| acc gcc gcg gtc acc gtc atc aag ccc aat ggg ccc att cca gga aca | 447 |
| Thr Ala Ala Val Thr Val Ile Lys Pro Asn Gly Pro Ile Pro Gly Thr | |
|  30                35              40 | |
| cag tcg acc gag act gcc aac gag ctg cct cgt ccc tac aag tgc cct | 495 |
| Gln Ser Thr Glu Thr Ala Asn Glu Leu Pro Arg Pro Tyr Lys Cys Pro | |
| 45                50              55              60 | |
| ctt tgc gac aag gct ttc cac cgc ctg gag cac cag acc agg cac att | 543 |
| Leu Cys Asp Lys Ala Phe His Arg Leu Glu His Gln Thr Arg His Ile | |
|                 65              70              75 | |
| cgc acc cac acg ggc gag aag ccc cat gcc tgc acc tcc att acc tgc | 591 |
| Arg Thr His Thr Gly Glu Lys Pro His Ala Cys Thr Ser Ile Thr Cys | |
|                     80              85              90 | |
| ttt ttt ttc taa tttacctgcc aatacaagac ttttttttt cttgttcgta | 643 |
| Phe Phe Phe | |
|           95 | |
| gggcggcggc tcctcagcgc taagatgcgt ttttacgtat ctcccctctg ggggtggcaa | 703 |
| aaatggaggg gggagggtca accttggaat caggctagat tgcctctttt tcttcttccc | 763 |
| cggtgtgtgt gtgtgagaga gagagtgtgt gagttgatgt gggggatggc gtccgtttgg | 823 |
| ctcgcttgga tggaatgcta tggaagagcg agaggcaaca ctgtattgtc actgtacagt | 883 |
| ggtaggttga cccatggagc attggtggga ttggtgaggt aacacaatct tgtgtggtcc | 943 |
| ctttctttcg agatacctga tggggaaaat tccgttgatg atgtgccggg ggatcttcac | 1003 |
| tttgatacga ggctgtatcc ctggtgctgt accttgactg tggctctatt gctacgatag | 1063 |
| agggtaggcc acatgaaggg gggcttcttt atttctttcc cttgtgatat ctgcacctga | 1123 |
| ttgcttgatg gaaaatgggc cgatgaatag aggcatgacg gcccttatg atacgaggaa | 1183 |
| gatgggggca ttttttttcg cgtgtgatga ctcgcttgat gacatgagga ggtgtggcat | 1243 |
| cagctccccg ttacacaaaa attctacgaa tagcgatctg gaaagacgct ctgttgaaaa | 1303 |
| aaaaa | 1308 |

<210> SEQ ID NO 7
<211> LENGTH: 95

```
<212> TYPE: PRT
<213> ORGANISM: Trichoderma reesei RUT-C30

<400> SEQUENCE: 7

Met Gln Arg Ala Gln Ser Ala Val Asp Phe Ser Asn Leu Leu Asn Pro
 1               5                  10                  15

Thr Ser Ala Ala Gly Gln Asp Ser Gly Ala Met Ser Thr Ala Ala Val
            20                  25                  30

Thr Val Ile Lys Pro Asn Gly Pro Ile Pro Gly Thr Gln Ser Thr Glu
        35                  40                  45

Thr Ala Asn Glu Leu Pro Arg Pro Tyr Lys Cys Pro Leu Cys Asp Lys
    50                  55                  60

Ala Phe His Arg Leu Glu His Gln Thr Arg His Ile Arg Thr His Thr
65                  70                  75                  80

Gly Glu Lys Pro His Ala Cys Thr Ser Ile Thr Cys Phe Phe Phe
                85                  90                  95

<210> SEQ ID NO 8
<211> LENGTH: 31
<212> TYPE: DNA
<213> ORGANISM: Trichoderma reesei RUT-C30

<400> SEQUENCE: 8
ggggaattca tagatggata gaaagagttg g                              31

<210> SEQ ID NO 9
<211> LENGTH: 47
<212> TYPE: DNA
<213> ORGANISM: Trichoderma reesei RUT-C30

<400> SEQUENCE: 9
ggggaattcc tcactatagg gagaccggcc tcgagttaat taagctt             47

<210> SEQ ID NO 10
<211> LENGTH: 23
<212> TYPE: DNA
<213> ORGANISM: Trichoderma reesei
<220> FEATURE:
<221> NAME/KEY: unsure
<222> LOCATION: (15)
<223> OTHER INFORMATION: a, c, g or t
<221> NAME/KEY: unsure
<222> LOCATION: (21)
<223> OTHER INFORMATION: a, c, g or t

<400> SEQUENCE: 10
ggcggatcct ytggngtrtc ngg                                       23

<210> SEQ ID NO 11
<211> LENGTH: 29
<212> TYPE: DNA
<213> ORGANISM: Trichoderma reesei
<220> FEATURE:
<221> NAME/KEY: unsure
<222> LOCATION: (12)
<223> OTHER INFORMATION: a, c, g or t
<221> NAME/KEY: unsure
<222> LOCATION: (18)
<223> OTHER INFORMATION: a, c, g or t
<221> NAME/KEY: unsure
<222> LOCATION: (21)
<223> OTHER INFORMATION: a, c, g or t

<400> SEQUENCE: 11
ggcggatcca cncayacngg ngaraarcc                                 29
```

<210> SEQ ID NO 12
<211> LENGTH: 23
<212> TYPE: DNA
<213> ORGANISM: Trichoderma harzianum
<220> FEATURE:
<221> NAME/KEY: unsure
<222> LOCATION: (15)
<223> OTHER INFORMATION: a, c, g or t
<221> NAME/KEY: unsure
<222> LOCATION: (21)
<223> OTHER INFORMATION: a, c, g or t

<400> SEQUENCE: 12
ggcggatcct ytggngtrtc ngg                                              23

<210> SEQ ID NO 13
<211> LENGTH: 29
<212> TYPE: DNA
<213> ORGANISM: Trichoderma harzianum
<220> FEATURE:
<221> NAME/KEY: unsure
<222> LOCATION: (12)
<223> OTHER INFORMATION: a, c, g or t
<221> NAME/KEY: unsure
<222> LOCATION: (27)
<223> OTHER INFORMATION: a, c, g or t

<400> SEQUENCE: 13
ggcggatcct nggrttrta rtakttngg                                         29

<210> SEQ ID NO 14
<211> LENGTH: 30
<212> TYPE: DNA
<213> ORGANISM: Trichoderma reesei

<400> SEQUENCE: 14
ggcggatcca tgcaacgagc acagtctgcc                                       30

<210> SEQ ID NO 15
<211> LENGTH: 30
<212> TYPE: DNA
<213> ORGANISM: Trichoderma reesei

<400> SEQUENCE: 15
ggcggatccc tacatggcat ccatgaggtc                                       30

<210> SEQ ID NO 16
<211> LENGTH: 17
<212> TYPE: DNA
<213> ORGANISM: Trichoderma reesei

<400> SEQUENCE: 16
atcagcagtc tctcctc                                                     17

<210> SEQ ID NO 17
<211> LENGTH: 17
<212> TYPE: DNA
<213> ORGANISM: Trichoderma reesei

<400> SEQUENCE: 17
actgtgttcc tggaatg                                                     17

<210> SEQ ID NO 18
<211> LENGTH: 31
<212> TYPE: DNA

```
<213> ORGANISM: Trichoderma reesei

<400> SEQUENCE: 18
ggggaattca tagatggata gaaagagttg g                                    31

<210> SEQ ID NO 19
<211> LENGTH: 47
<212> TYPE: DNA
<213> ORGANISM: Trichoderma reesei

<400> SEQUENCE: 19
ggggaattcc tcactatagg gagaccggcc tcgagttaat taagctt                   47

<210> SEQ ID NO 20
<211> LENGTH: 6
<212> TYPE: DNA
<213> ORGANISM: Trichoderma reesei
<220> FEATURE:
<221> NAME/KEY: polyA_signal
<222> LOCATION: (1)..(6)
<223> OTHER INFORMATION: T. reesei cre1 gene at 263, 494
      and 665 bp and T. harzianum cre1 gene at 234, 445 and
      735 after the CDS

<400> SEQUENCE: 20 aaatat                                                                6

<210> SEQ ID NO 21
<211> LENGTH: 6
<212> TYPE: DNA
<213> ORGANISM: Trichoderma harzianum
<220> FEATURE:
<221> NAME/KEY: polyA_signal
<222> LOCATION: (1)..(6)
<223> OTHER INFORMATION: T. reesei cre1 gene at 263, 494 and
      665 bp and T. harzianum cre1 gene at 234, 445 and  735 after the
      CDS

<400> SEQUENCE: 21 taatat                                                                6
```

PROCESS FOR MODIFYING GLUCOSE REPRESSION

FIELD OF THE INVENTION

The present invention relates to recombinant-DNA-technology, and particularly to genes involved in the control of basic metabolic processes in fungi. The invention specifically provides mutated glucose repressor genes to be transformed to fungal strains in order to render the strains capable of producing elevated amounts of secreted proteins without reducing the viability of the strain.

BACKGROUND OF THE INVENTION

Carbon catabolite repression is a major mechanism controlling metabolic processes of both prokaryotic and eukaryotic microbes. In the presence of readily metabolizable carbon sources such as glucose the expression of structural genes required for utilization of other alternative carbon sources is decreased. Cellulases and other secreted hydrolase enzymes are proteins whose production is repressed by glucose. In general, glucose repression is mediated through the action of specific proteins that regulate transcription by binding promoter sequences of the target genes (Trumbly, 1992).

The creA gene of the filamentous fungus *Aspergillus nidulans* is a well characterized regulatory gene mediating carbon catabolite repression (Arst and Bailey, 1977). The central role of the CREA protein of *A. nidulans* in carbon catabolite repression has been verified extensively by genetic (Arst et al., 1990) and molecular analysis (Mathieu and Felenbok, 1994). Mutations of the creA gene are recessive to the wild type gene. Some of the mutants have abnormal morphology (Arst et al., 1990), and haploid *A. nidulans* creA$^-$ strains constructed by genetic engineering, lacking the entire protein coding region of the creA gene (Dowzer and Kelly, 1991) have extremely reduced viability. Additionally, the carbon metabolism in the mutant strains is altered in different ways. The most extreme of the in vivo isolated creA mutants with respect to growth impairment is the creA30 mutation that additionally results in formation of an abnormally compact colony. Molecular analysis of the creA30 gene sequence revealed that the gene is truncated at the 3' end corresponding to a protein having two intact zinc fingers but lacking the sequences C-terminal to the DNA-binding region (Dowzer and Kelly, 1991). This is the most extreme mutation of creA described so far.

The CREA protein has two zinc fingers of $C_2H_2$ type involved in base recognition. The CREA fingers are strikingly similar to the ones of the glucose repressor MIG1 of *Saccharomyces cerevisiae*. In addition, the C-terminal one of the two fingers has significant similarities with the fingers found in mammalian early growth response proteins involved in developmental regulation. Obvious sequence similarities in other parts of the proteins are, however, missing Nehlin and Ronne, 1990). Another yeast gene RGR1, is also involved in glucose repression. The phenotypic effects of the rgr1-1 mutation somewhat resemble those of crea mutant alleles, and a RGR1$^-$ strain is not viable (Sakai et al., 1990).

Similarities in carbon catabolite repression have thus been found between yeast and filamentous fungi, and some of the basic features of glucose repression are probably universal in eukaryotic microorganisms. Considering that crea has such a central role in Aspergillus as a regulator of different sets of genes that are subject to carbon catabolite repression, it is likely that similar mechanisms mediating glucose repression are found in related organisms. Besides *A. nidulans*, the creA gene has so far been isolated only from the closely related species, *A. niger* (Drysdale et al., 1993).

DESCRIPTION OF THE INVENTION

In order to address the role of creA in other filamentous fungi and especially in relation to cellulase expression, we have isolated the creA equivalent cre1 from the filamentous fungus *Trichoderma reesei* which is one of the most extensively studied cellulolytic organisms (reviewed e.g. by Nevalainen and Penttilä, 1995). The production of cellulases is dependent on the carbon source available, and glucose repression is very tight. The expression level of the major cellobiohydrolase 1 (cbh1) is up to several thousand fold higher on media containing inducing carbon sources such as cellulose or sophorose compared with glucose containing media (Penttilä et al., 1993). Deletion analysis of the cbh1 promoter has suggested that a crea equivalent would be involved in glucose repression of cellulase expression in *T. reesei* (Penttilä et al., 1993). In addition to the cre1 gene of *T. reesei*, we isolated the same gene from the related species *T. harzianum*. The expression studies of the *T. reesei* cre1 gene revealed unexpected indication of autoregulation. Furthermore, a hypercellulolytic *T. reesei* strain was found to express a truncated form of the cre1 gene with an unexpected structure and properties. The truncated cre1 gene of the strain *T. reesei* Rut-C30 was named cre1-1.

The present invention thus provides a mutated fungal glucose repressor gene which, when transformed to a fungal strain maintains said strain fully viable and renders said strain capable of producing elevated amounts of secreted proteins, even in the presence of glucose. Furthermore, this strain has an altered glucose uptake, as well as altered growth characteristics on certain nitrogen sources.

Consequently, a further object of this invention is the use of said gene in a process for enhancing the production of secreted proteins in a fungal host, which process comprises transforming the truncated cre1 gene according to the invention into a suitable fungal host, and replacing the existing cre1 gene, cultivating the transformed host in a suitable growth medium comprising glucose, and recovering the protein produced.

According to the present invention it is also possible to control the growth rate of a fungus by regulating the type of nitrogen source and the amount of glucose in the medium.

Fungal strains transformed with the truncated cre1 gene are also provided.

Unexpected results were obtained when studying the expression of the *T. reesei* cre1 gene. If glucose repression mediated through CREI was regulated at the level of cre1 transcription, one would expect increase in transcription in the presence of glucose. However, high expression of cre1 does not correlate positively with glucose repression, in fact when glucose is present in repressing amounts the level of cre1 transcript is relatively low, and higher on the neutral carbon sources sorbitol and glycerol, and on cellulose. Furthermore, addition of glucose to cultivations carried out on the neutral carbon sources reduced the level of cre1 transcript, which is indicative of autoregulation.

Further indication for autoregulation was obtained when studying expression of the mutated form of the glucose repressor gene cre, i.e. cre1-1 of the hypercellulolytic *T. reesei* strain Rut-C30. Nearly 80% of the protein coding region, including one of the two zinc fingers, is deleted as compared to the "native" cre1 gene of *T. reesei* QM9414. The *T. reesei* cre1-1 mutation could suggest that the N-terminal zinc finger could be sufficient for DNA-binding and thus retaining most of the viability of the fungus. However, the strain Rut-C30 produces relatively high levels of cre1-1 mRNA also on glucose medium compared with the strain QM9414. Assuming that CREI down regulates its own expression when growing on glucose medium, the abundancy of cre1-1 mRNA may be explained by the inability of the CREI-1 protein to bind the target sequences in its own promoter, or by the inability of the truncated form of the protein to confer repression of the gene. This should hold true also for other genes regulated by cre1, which is here shown by derepression of the cellulase gene cbh1.

The high cellulase cbh1 mRNA levels detected in the presence of glucose in combination with the mutation resulting in the truncated form of cre1, support true carbon catabolite derepression in this strain. The results obtained with Rut-C30 now further support the suggestion that cellulase expression is under control of carbon catabolite repression mediated at least partially by CREI. It is likely that a similar situation holds true for other filamentous fungi, and furthermore that also other hydrolytic enzymes involved in utilization of plant polymeric substrates could be regulated by CREI/CREA proteins.

By replacing the cre1 gene in *T. reesei* QM9414 with the mutated gene cre1-1 it is possible to construct a strain expressing the cre1-1 and transfer the glucose derepressed phenotype of Rut-C30 into another Trichoderma strain. A strain constructed in this way is fully viable, and is further able to produce secreted proteins in the presence of glucose. The properties are extremely useful in biotechnical processes when producing secreted proteins.

We have also transformed the native full length cre1 gene into the Rut-C30 strain. The characteristics of the new strain obtained indicated that the mutated gene cre1-1 of Rut-C30 has a function partly allowing transcription of a cellulase gene suggesting competition between the products of cre1 and cre1-1 genes. Alternatively, an additional mutation in Rut-C30 is partly taking part in glucose derepression in addition to cre1.

Other highly unexpected results are also described. It is for the first time shown that glucose consumption from the medium is under cre control and particularly so that some residual glucose can remain completely unutilized in a strain mutated in cre. This result shows that several mutant forms of cre can now be generated and transferred to fungal strains, which will result in changed glucose consumption of the strain. It is noteworthy that glucose containing cultures and for instance fed-batch cultivations with the necessity of careful control of glucose amount are generally used in biotechnical processes for protein production. Using strains harboring cre mutations allows now a new type of process control. Another unexpected result shown is that growth rate modulation is under cre control in a way dependent on the type of nitrogen source provided for the fungus. This allows the growth rate, however retaining the strain fully viable, to be controlled in biotechnical processes.

BRIEF DESCRIPTION OF THE DRAWINGS

FIG. 1 Alignment of the amino acid sequences of three *T. reesei* CREI proteins (Rut-C30 (SEQ ID NO:7), VTT-D-80133 (SEQ ID NO:5) and QM9414) (SEQ ID NO:5) as well as of *T. harzianum* T3 (SEQ ID NO:2). The domain containing the two zinc fingers is underlined in the T3 sequence.

EXPERIMENTAL

Materials and Methods Used

Fungal Strains

Figure 2:
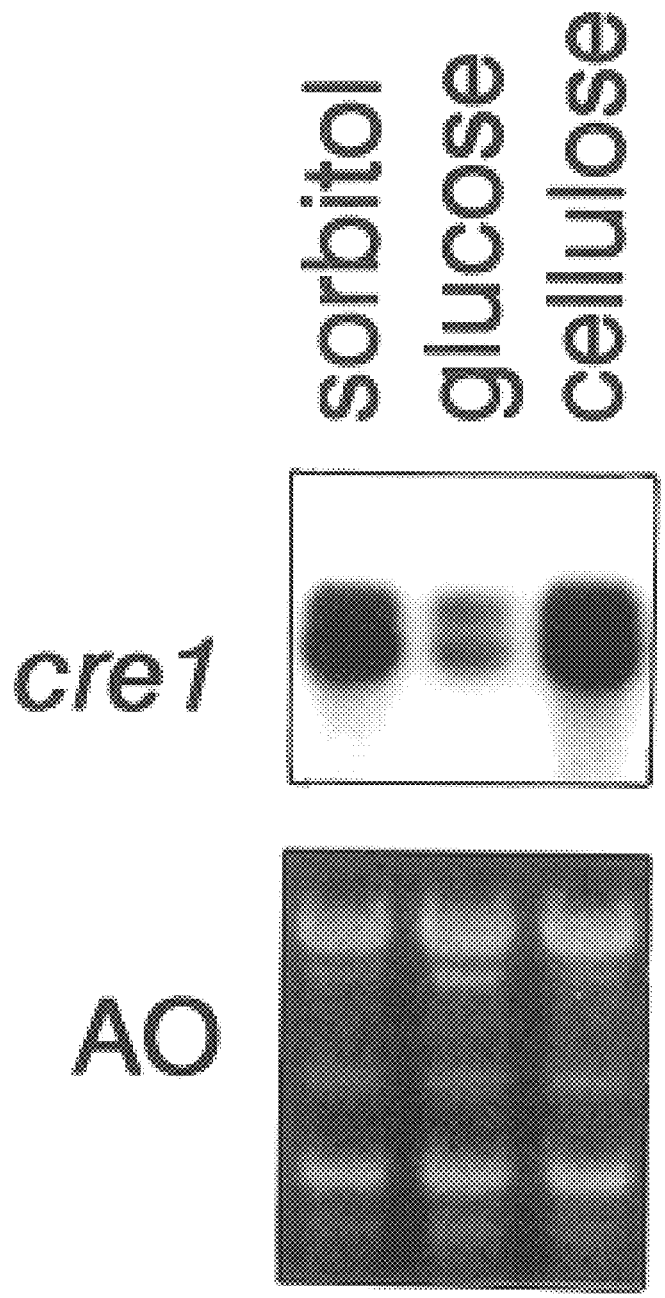
FIG. 2 Expression of cre1 in *T. reesei* strain QM9414 cultivated on minimal medium supplemented with either 2% sorbitol, 5% glucose or 3% Solka floc cellulose at the cultivation times indicated. 2 µg of total RNA was loaded on gel. Prior to blotting and hybridization the gel was stained with acridine orange (AO) to visualize the amount of RNA loaded. Hybridization probe was a 600 bp long internal PCR fragment of the cre1 (see experimental).

*T. reesei* strain QM9414 (VTT-D-74075, ATCC 26921) (Mandels et al. 1971) was used for gene expression studies, isolation of RNA, and as a source of DNA for preparation of PCR fragments used as a probe. DNA of *T. reesei* strain VTT-D-80133 (Bailey & Nevalainen 1981), a mutant strain of QM9414 with increased cellulolytic activity, was used in the construction of the chromosomal gene library. *T. reesei* Rut-C30 (ATCC 56765), a hypercellulolytic mutant strain (Montenecourt and Eveleigh 1979) was cultivated for isolation of DNA and RNA. DNA extracted from the *T. harzianum* isolate T3 (Wolffhechel, H., 1989) was used for construction of a genomic lambda library.

Cultivation Conditions

For RNA isolation, 50 ml of each cultivation media in 250 ml conical flasks were inoculated with $10^7$ spores and incubated in a rotary shaker at 200 rpm at 28° C. Trichoderma minimal medium (TMM) contained $KH_2PO_4$ 15 g/l, $(NH_4)_2SO_4$ 5 g/l, $FeSO_4 \times 7H_2O$ 5 mg/l, $MnSO_4 \times H_2O$ 1.6 mg/l, $ZnSO_4 \times H_2O$ 1.4 mg/l, $COCl_2 \times 6H_2O$ 3.7 mg/l, $MgSO_4$ 0.6 g/l, $CaCd_2$ 0.6 g/l, pH was adjusted to 4.8. Proteose peptone 2 g/l was added to certain culture media as indicated in text. This medium was used throughout the study supplemented with the appropriate carbon source, either 20 g/l (sorbitol, glycerol, glucose) or 50 g/l (glucose). In certain sorbitol or glycerol cultivations glucose was added into final concentration of 2% by adding 4 ml of 25% glucose into 50 ml of cultivation media after 72 h of growth. Similarly, 1 mM α-sophorose (Serva) was added into the culture medium twice, at 72 and 82 hours of growth. Cellulose medium was TMM supplemented with Solka floc cellulose 30 g/l and distiller's spent grain 15 g/l and the pH was adjusted to 5.0. Mycelia was harvested from culture medium by filtration through GF/B glass microfibre filters (Whatman), washed with sterile water and stored at −70° C.

For DNA isolation, the cultivation was as described above except that TMM was supplemented with 2% glucose and 0.2% proteose peptone (Difco) and mycelia was freeze-dried after harvesting and stored at −20° C. For preparation of solid media, the pH of TMM was adjusted to 5.5 and 2% agar was added. 0.1% Triton X-100 was used to restrict spreading of the colonies.

Preparation of cre1 Probes for Gene Cloning and Expression Studies

To clone the cre1 genes of Trichoderma several redundant oligodeoxyribonucleotides were designed based on Aspergillus CREA protein sequences, synthesized and used as primers with Trichoderma chromosomal DNA as a template in a PCR reaction. The functional primer pair used for *T. reesei* was 5'GGCGGATCCT(C,T)TGGNGT(G,A)TCNGG (antisense) (SEQ ID NO:10) and 5'GGCGGATCCACNCA(C,T)ACNGGNGA(A,G)AA(A,G)CC (sense) (SEQ ID NO:11) and for *T. harzianum* 5'GGCGGATCCT(C,T)TGGNGT(G,A)TCNGG (antisense (SEQ ID NO:12) and 5'GGCGGATCCTTNGG(G,A)TT(G,A)TA(A,G)TA(T,G)TTNGG (sense) (SEQ ID NO:13). BamHI cleavage sites were included at the 5' ends of the primers to facilitate cloning of the amplified fragment. PCR cycling used in both reactions was as follows: four cycles of repeated denaturation at 96° C. 1 min—annealing at 37° C. 30 sec—polymerization at 72° C. 1 min followed by 25 cycles of repeated denaturation at 96° C. 1 min—annealing at 55° C. 1 min—polymerization at 72° C. 1 min.

The PCR products of expected size, around 600–700 bp, were cut with BamHI and ligated to BamHI linearized pUC19 vector, and transformed into *E. coli* DH5α. The resulting plasmids were isolated using standard methods and sequenced to demonstrate cloning of Trichoderma cre1 fragments. For hybridization, the cre1 fragments (600 bp for *T. reesei*, 660 bp for *T. harzianum*) were released from the plasmids by BamHI digestion, purified from agarose gel by phenol extraction and labelled using Random Primed DNA Labeling Kit (Boehringer Mannheim) and α-$^{32}$P-dCTP (Amersham) to a specific activity of $10^8$ cpm/μg.

The probe fragment corresponding to the full length protein coding region of the *T. reesei* cre1 gene was prepared by PCR using the *T. reesei* cre1 cDNA clone as a template. The primers used, 5'GGCGGATCCATGCAACGAGCACAGTCIGCC (sense) (SEQ ID NO:14), and 5'GGCGGATCCCTACATGGCATCCATGAGGTC (antisense) (SEQ ID NO:15), were complementary to the 5' and 3' ends of the protein coding region of the cre1 gene and contained BamHI cleavage sites at the ends to facilitate cloning. PCR cycling was repeated 25 times as follows: 94° C. 45 sec—55° C. 30 sec.—72° C. 2 min.

The 294 bp long probe fragment corresponding to the nucleotides from −158 to +136 of the *T. reesei* cre1 was synthesized by PCR using the cDNA clone as a template and the primers 5ATCAGCAGTCTCTCCTC (sense) (SEQ ID NO:16), and 5'ACTGTGTICCTGGAATG (antisense) (SEQ ID NO:17). The PCR cycling was repeated 25 times the following way: 95° C. 45 sec—42° C. 30 sec—72° C. 45 sec.

DynaZyme™ DNA-polymerase was used in each PCR reaction described above in the reaction conditions recommended by the manufacturer (Finnzymes Oy, Espoo, Finland).

Full length cbh1 cDNA was obtained as an EcoRI-HindIII fragment from pTTC01 (Penttilä et al. 1988) and the probe was prepared as described above.

Construction of Genomic Libraries and Isolation of the cre1 Genes

In order to clone the *T. reesei* chromosomal cre1 gene, the genomic cosmid library of *T. reesei* VTT-D-80133 (Mäntylä et al. 1992) was plated out on ampicillin plates and after overnight incubation bacterial colonies were transferred to nitrocellulose membranes and screened with the 600 bp long *T. reesei* cre1 probe using colony hybridization. Colonies giving a positive hybridization signal were purified and cosmid DNA was prepared using standard plasmid isolation procedures. Cosmid DNA carrying the cre1 gene was partially restriction mapped and analyzed by Southern hybridization. A 6.4 kb SalI-HindIII restriction fragment containing the entire protein coding region with flanking regions was subcloned for sequencing into pSP73 plasmid vector (Promega) digested with SalI-HindIII. The plasmid was designated pMI-41.

In order to clone the cre1 gene of the *T. harzianum* isolate T3, chromosomal DNA was prepared according to Raeder & Broda (1985), partially digested with Sau3A and size fractionated by sucrose gradient centrifugation (Sambrook et al. 1989), and DNA fragments of about 22 kb were ligated to BamHI digested, phosphatase treated lambda DASH™ vector arms and the ligation mixture was packaged into lambda particles using Gigapack II Gold Packaging Extract (Stratagene). The lambda particles were used to infect appropriate *E. coli* host cells, and the library was screened using the 660 bp long *T. harzianum* cre1 fragment as a probe, and positive clones were isolated and purified according to manufacturer's instructions (Stratagene). Bacteriophages were purified using a method based on the general procedure described in Sambrook et al. (1989) with the following modifications: DNAseI treatment was omitted and phage particles released from lysed host cells were precipitated using PEG6000, dissolved in SM and extracted with chloroform, pelleted by centrifugation at 25 000 rpm in Kontron TST41.14 rotor for 2 h, and again dissolved in SM. ILunbda DNA was isolated by digesting the phage particles with proteinase K followed by phenol extraction and ethanol precipitation. DNA of the lambda clones containing *E. harzianum* cre1 gene, were partially restriction mapped and analysed by Southern hybridization. Two EcoRV restriction fragments, one of 3 kb containing the 5' end and the other of 4.9 kb containing the 3' end with flanking regions, both giving a positive hybridization signal with cre1 probe, were subcloned into EcoRV cut, phosphatase treated plasmid vector pSP73 (Promega) for sequencing.

In order to isolate cre1 cDNA clones, the cDNA library of the *T. reesei* strain QM9414 constructed into lambda uniZAP XR vector (Nakari et al. 1993) was screened with the 600 bp long *T. reesei* cre1 probe prepared as described above. The cDNA library of the *T. reesei* strain Rut-C30 (Stalbrand et al., 1995) was screened using the full length cre1 protein coding region as a probe. Bacteriophage DNA of positive clones were in vivo excised and converted into plasmid form according to the instructions of Stratagene.

Southern, Dot Blot and Colony Hybridizations

For colony hybridization, bacterial colonies or lambda plaques were transferred from agar plates onto nitrocellulose membranes (Schleicher & Schuell B A 85) by placing the membrane on the plate for 1 min. The membrane was placed on filter paper soaked in denaturing solution (0.5M NaOH—1.5M NaCa) for 7 min and then on filter paper soaked in neutralizing solution (1.5 M NaCl—0.5 M Tris-HCl pH 7.5) for 2×3 min, whereafter the membranes were soaked in 2×SSC, and DNA was fixed by baking the membranes at 80° C. for 2 h. To remove excess bacterial debris the membranes were washed prior to hybridization in 50 mM Tris pH 8—1M NaCl—1 mM EDTA—0.1% SDS at 42° C. for 1 h. Hybridization was carried out in 50% formamide—5× Denhardt's-5×SSPE—0.1% SDS—100 $\mu$g/ml herring sperm DNA-1 $\mu$g/ml polyA DNA at 42° C. overnight with $10^6$ cpm of probe per ml of hybridization solution. After hybridization the membranes were washed in 2×SSC—0.1% SDS at room temperature followed by a wash in 1×SSC—0.1% SDS at 68° C. for 1 h, and exposed to Kodak XAR-5 X-ray film at −70° C.

For Southern analysis 2 $\mu$g of Trichoderma chromosomal DNA was completely digested with restriction enzymes (Boehringer Mannheim), the resulting DNA fragments were separated by electrophoresis in 0.8% agarose gel and DNA was capillary blotted onto Hybond N nylon membrane. Conditions for hybridization were as described for colony hybridization, except that the post hybridization washes were performed in 2×SSC at room temperature 2×5 min followed by a wash in 1×SSC—0.1% SDS at 68° C. for 60 min.

For DNA dot blot hybridization, 1 $\mu$g of chromosomal DNA was denatured in 0.4 M NaOH for 10 min and neutralized by addition of an equal volume of 2 M ammonium acetate pH7, and dot blotted onto a Hybond N nylon membrane. Hybridization and washing were done as described for Southern analysis.

Northern Analysis

Total fungal RNA was isolated according to Chirgwin et al. (1979), glyoxylated and electrophoresed in 1% agarose gel in 10 mM Na-phosphate buffer pH 7.0 according to Maniatis et al. (1982). RNA ladder (BRL) containing RNA molecules of known length were used as molecular weight markers. The gel was stained with acridine orange (15 $\mu$g/ml) for 15 min in 10 mM phosphate buffer to visualize RNA and de-stained for 3 h in 10 mM phosphate buffer. Thereafter RNA was blotted onto Hybond™ N nylon membranes (Amersham) by capillary blotting in 20×SSC. Hybridization was carried out in 50% formamide—10% dextran sulphate—1% SDS—1M NaCl—125 $\mu$g/ml denatured herring sperm DNA at 42° C. overnight using $10^6$ cpm of probe per ml of hybridization solution. The membranes were washed at 42° C. in 5×SSPE, twice in 1×SSPE—0.1% SDS, twice in 0.1×SSPE—0.1% SDS, each wash lasting 15 min, and exposed to Kodak XAR-5 X-ray film at −70° C.

Plasmid Constructions

Figure 5A:
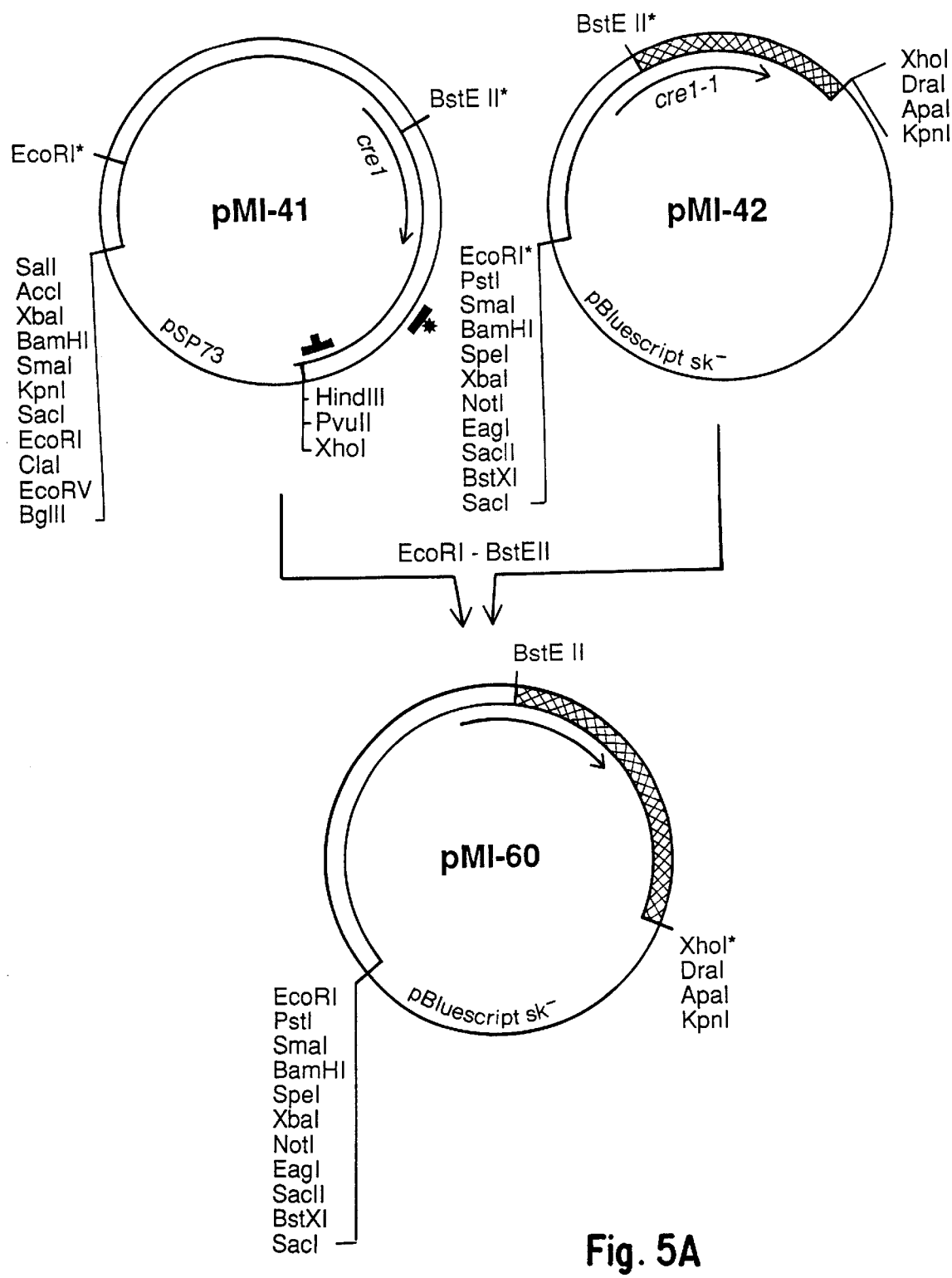
FIG. 5 Construction of the vector for replacement of QM9414 cre1 by cre1-1 of Rut-C30. Relevant restriction enzyme recognition sites used in the cloning steps are indicated with stars (*). The PCR primers are 5'GGGGAAT-TCATAGATGGATAGAAAGAGTTGG (sense) (SEQ ID NO:8) and 5'GGGGAATTCCTCACTATAGGGAGACCG-GCCTCGAGTTAATTAAGCTT (antisense) (SEQ ID NO:9)
Figure 5B:
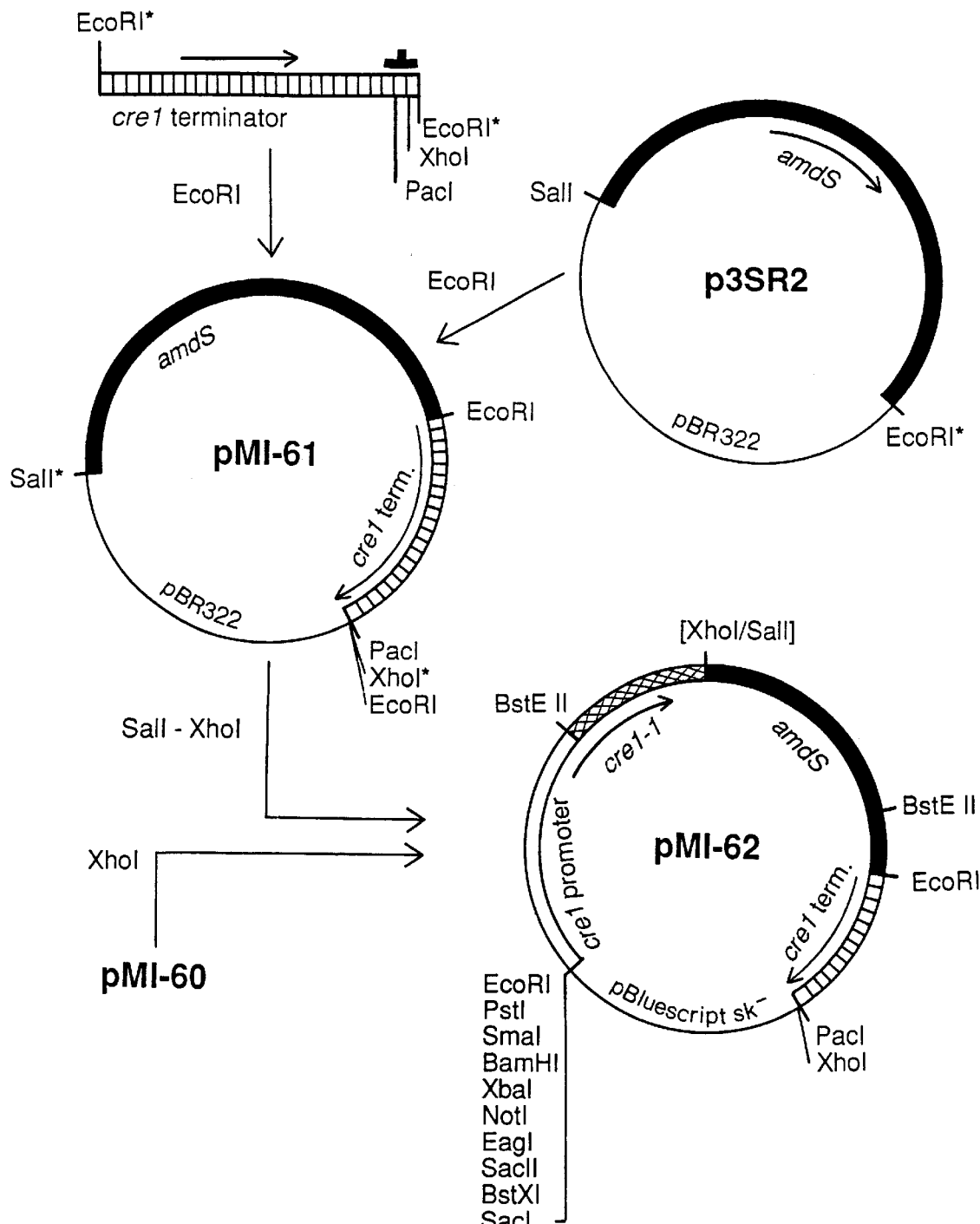

For replacement of cre1 of *T. reesei* QM9414 by the mutated gene cre1-1 of *T. reesei* Rut-C30 an expression vector pMI-62 was constructed (see also FIG. 5) in the plasmid pBluescript SK⁻. pMI-62 was constructed as follows: 5'-sequences of cre1 were obtained from pMI-41 as the 3 kb EcoRI-BstEII fragment that was joined in frame to the BstEII-EcoRI fragment of cre1-1 cDNA from plasmid pMI-42 resulting in plasmid pMI-60. A 1.4 kb fragment of cre1 terminator, beginning 50 bp downstream of the translation stop codon and ending at the naturally occurring HindIII site, was amplified by PCR using pMI-41 as a template and sequence specific primers that were tailed with EcoRI sites to facilitate cloning of fragment. The PCR primer sequences corresponding to nucleotides starting from 50 bp downstream of cre1 protein coding region and to vector sequences surrounding the single HindIII site were 5'GGGGAATTCATAGATGGATAGAAAGAGTTGG (SEQ ID NO:18) and 5'GGGGAATTCCTCACTATAGG-GAGACCGGCCTCGAGTTAATTAAGCTT (SEQ ID NO:19), respectively. The PCR amplified cre1 terminator fragment was EcoRI cut and cloned to plasmid p3SR2 linearised using EcoRI, resulting in the plasmid pMI-61. pMI-60 was cut using XhoI and pMI-61 using SalI-XhoI and the fragment containing the amdS gene and cre1 terminator was ligated to XhoI linearized pMI-60 resulting in plasmid pMI-62.

Transformation of Trichoderma

*Trichoderma reesei* was transformed according to Penttilä et al. (1987).

Immunological Detection of CBHI

Production of CBHI into culture medium was detected using antibodies. 200 $\mu$l and 40 $\mu$l aliquots of culture medium were dot blotted onto a nitrocellulose membrane. The membrane was incubated in 3% non fat dried milk—TBS (10 mM Tris-HCl pH8—150 mM NaCl) at 37° C. for 10 min, washed in TBS 3×10 min. The membrane was incubated in TBS containing monoclonal anti-CBHI-antibody CI-258 (Aho et al. 1991) for 1 h at room temperature and washed in TBS. Then the membrane was transferred to TBS containing anti-mouse polyvalent immunoglobulins conjugated with alkaline phosphatase (Sigma A-0162) and incubated for 1 h at room temperature. The bound antibody was detected using the NBT and BCIP reagents (Promega) in a solution containing 100 mM Tris-HCl pH 9.5—100 mM NaCl—5 mM $MgCl_2$.

Other Methods

The genomic cre1 genes were sequenced from both strands using Sanger's dideoxynucleotide method, sequence specific primers and Sequenase version 2 polymerase (USB). cre1 cDNA clones were sequenced from one strand. All other techniques not described in detail were carried out using standard methods (e.g. Sambrook et al. 1989). PC/Gene nucleic acid and protein sequence analysis software release 6.80 (Intelligenetics Inc.) was used for sequence manipulations.

EXAMPLE 1

Isolation and Characterization of the *T. reesei* and *T. harzianum* cre1 Genes

Fragments of the cre1 genes of *T. reesei* and *T. harzianum* were amplified from chromosomal DNAs by polymerase chain reaction (PCR) using degenerate oligodeoxyribonucleotide primers designed on the basis of the Aspergillus CREA sequence information. Primers, which gave rise to inserts with similarity to the A. nidulans creA gene were complementary at the 5' end with the zinc finger region or the linker region connecting the two fingers, and at the 3' end with the proline rich region showing similarity to the RGR1 protein of yeast (see later). The cre1 fragments were used as hybridization probes to isolate chromosomal copies of the cre1 genes of the T. reesei strain VTT-D-80133 and T. harzianum T3. The clones were restriction mapped and sequenced from subcloned fragments.

The T. reesei cre1 gene contains an open reading frame (ORF) of 1206 nucleotides (SEQ ID NO:3) which can be translated to a 402 amino acids long protein (SEQ ID NO:5), and the T. harzianum gene (SEQ. ID. NO: 1) an ORF of 1227 bp, encoding 409 amino acids. The nucleotide sequences of these two Trichoderma cre1 genes show 89% identity within the predicted protein coding region.

In addition to the chromosomal copy, which was isolated from the T. reesei strain VTT-D-80133 (SEQ. ID. NO. 3), a cDNA copy was isolated from the T. reesei strain QM9414 (SEQ. ID. NO. 4). The only difference in cre1 nucleotide sequence observed between these two strains was at position 140, where C is found in QM9414 instead of T in VTT-D-80133 which changes amino acid no 47 from threonine (QM9414) to isoleucine (VTT-D-80133). In the T. harzianum CREI, threonine is found at this position. Sequencing of the cDNA copy confirmed that there are no introns in the T. reesei cre1 gene.

Sequencing of the 3' ends of nine T. reesei cre1 cDNA clones showed that the mRNA was equally often cleaved at two different regions separated by approximately 170 bp at the 3' end of the cre1 transcript. There is some heterogeneity in the cleavage sites, the shorter forms of the cDNAs end 281–288 bp, and the longer ones 450–454 bp after the protein coding region. Sequences of the chromosomal copies show several putative polyadenylation signals, AAATAT (SEQ ID NO:20) or TAATAT (SEQ ID NO:21), which are located in the T. reesei cre1 gene at 263, 494 and 665 bp, in the T. harzianum cre1 at 234, 445 and 735 bp after the protein coding region.

The codon usage of the Trichoderma cre1 genes is biased against A in the third position, which is typical for filamentous fungi (Unkles 1992). The codon preference is more biased than that of cellulase genes of T. reesei but not as biased as for instance that of the translation elongation factor tef1 (Nakari et al. 1993) or the phosphoglycerate kinase gene pgk1 (Vanhanen et al. 1989).

EXAMPLE 2

CREI Amino Acid Sequence Comparisons

The deduced CREI amino acid sequences of T. reesei and T. harzianum show 95% similarity (92.5% identity) (FIG. 1) (SEQ ID NOS:5 and 2 respectively). When compared with the CREA protein sequences of A. nidulans and A. niger 72% overall similarity (46% identity) is obtained.

One of the two best conserved regions between Trichoderma and Aspergillus localizes in the DNA-binding motif, the $C_2H_2$ type zinc finger which is almost perfectly conserved throughout the 57 aa long region. Interestingly, the amino acid sequences surrounding the zinc finger domain differ between the Aspergillus and Trichoderma proteins. On the amino terminal side of the finger, 13 amino acids are missing in both of the Trichoderma proteins compared with the Aspergillus sequences. On the carboxy terminal side an 8–9 aa long alanine stretch found in the Aspergillus CREA proteins is replaced by histidine and glutamine residues in Trichoderma.

The other equally well conserved region is found further downstream. Within this region 39 out of 41 amino acids are identical between the Trichoderma and Aspergillus CREI/CREA proteins. Characteristic to this part of the CREI/CREA proteins is the content of about 25% proline, 25% serine and 12% threonine. The sequence shows similarity to the glucose repressor protein RGR1 of yeast (Sakai et al. 1990).

EXAMPLE 3

Expression of T. reesei cre1 is Dependent on the Carbon Source Available

Northern analysis shows that T. reesei QM9414 produces two major cre1 transcripts of 1.85 kb and 2 kb and a faint one of 2.6 kb, visible only after a prolonged exposure (FIG. 2). These were detected in all the cultivation conditions studied with approximately the same relative abundancy. These features are in good correlation with the observed size difference of 170 bp of the cDNA clones analysed (see above) and demonstrate together with the Southern analysis that both the two major transcripts are products of a single gene.

Because the T. reesei cellulase genes are subject to glucose repression, it was of interest to study expression of cre1 in conditions relevant for cellulase expression. The cultivations were carried out in shake flasks on media containing either glucose, Solka floc cellulose, which is an efficient inducer, or on sorbitol which is a neutral carbon source in respect to cellulase expression (Penttila et al., 1993). Northern analysis revealed that the steady state levels of cre1 transcript show clear variation in these different cultivation conditions in repeated experiments. In contrast to expectation, cre1 mRNA levels were surprisingly high on the inducing carbon source cellulose. Moreover, they were lower on glucose than on cellulose or sorbitol medium (FIG. 2). Thus, the expression of cre1 is regulated by the carbon source available.

Figure 3:
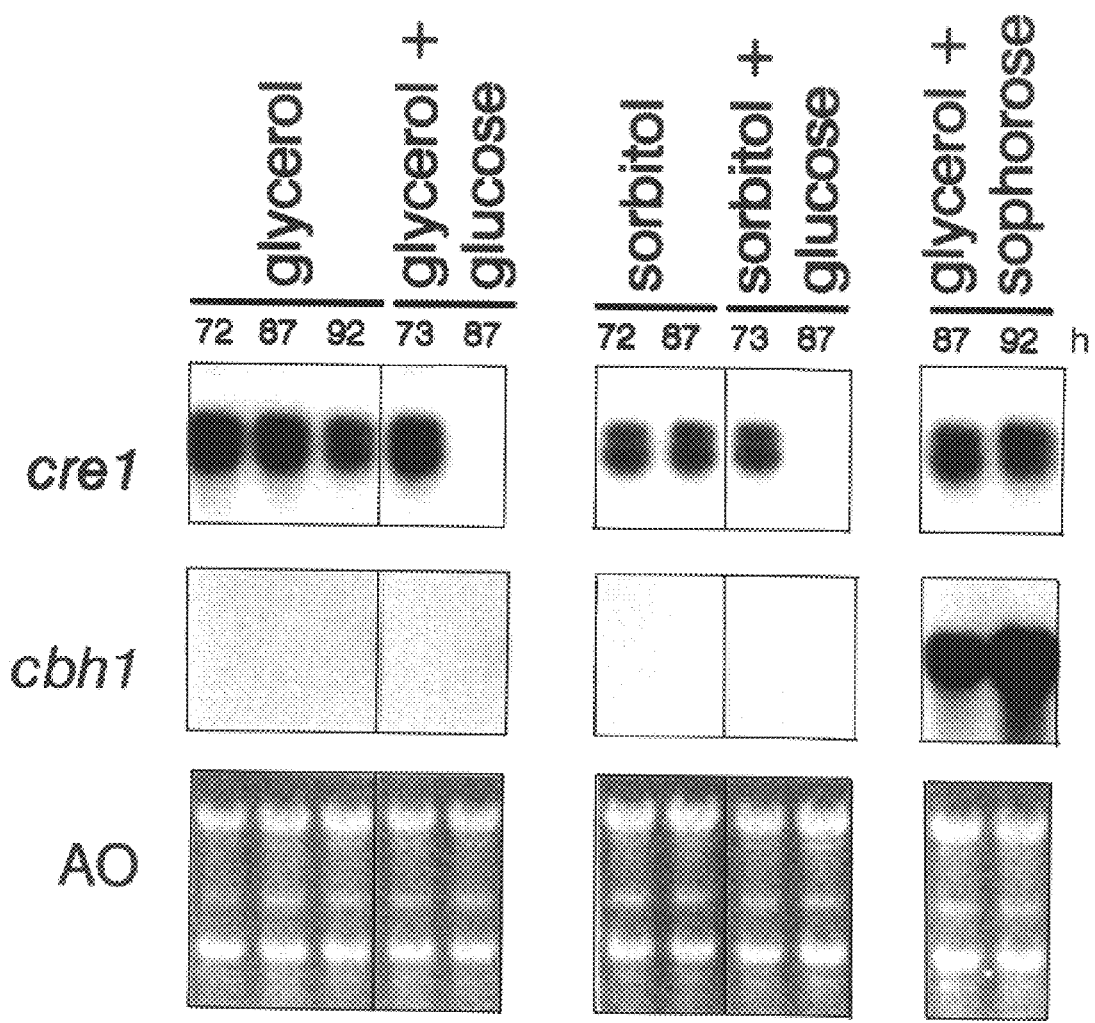
FIG. 3 Effect of different carbon sources on the expression of cre1 and cbh1 of *T. reesei* QM9414. Cultivations were carried out for 72–92 h as indicated on minimal medium supplemented with either 2% sorbitol or 2% glycerol. At 72 h, glucose was added to 2% into certain sorbitol and glycerol cultures and incubation was continued for 1 h (total cultivation time 73 h) or 15 h (total cultivation time 87 h). Similarly, 1 mM sophorose was added into glycerol cultures twice, at 72 h and 82 h, and the incubation was continued for 15 h (total 87 b) or 20 h (total 90 h). Northern blot was prepared and hybridized as described in the legend to FIG. 2.

Consequently, the effect of glucose on cre1 transcription was studied in more detail and a new series of cultivations was carried out. The fungus was grown for 72 h on a medium containing either sorbitol or glycerol, both neutral carbon sources in respect to cellulase expression, whereafter glucose was added to 2%. At this point of cultivation the fungus has not yet utilized all sorbitol or glycerol. Mycelia were collected for RNA isolation 1 h and 15 h after the addition of glucose. In control mycelia grown on glycerol or sorbitol medium without glucose addition, cre1 mRNA was equally abundant at different time points during the cultivation (FIG. 3). The levels of cre1 mRNA remained unchanged also one hour after glucose addition to the sorbitol and glycerol cultures. However, after overnight incubation in the presence of glucose, cre1 mRNA levels were significantly decreased compared with the sorbitol and glycerol cultures where glucose was not added. For comparison, the addition of sophorose, an efficient inducer of cellulase expression, into sorbitol or glycerol cultivations did not affect cre1 transcript levels at the time points studied (FIG. 3).

EXAMPLE 4

The Truncated Form of cre1 Expressed by the Hypercellulolytic T. reesei Strain Rut-C30

Northern analysis carried out for Rut-C30 using the PCR-amplified 600 bp long probe specific for the central part of the cre1 gene gave no expression. When Southern analysis of genomic DNA cut with restriction enzymes EcoRI, SalI, AccI, PvuII and SphI was carried out using the complete protein coding region of cre1 as a probe it revealed weak hybridization to the probe and a pattern differing from that of the strain QM9414 (data not shown). Subsequently the full length cre1 probe was used to isolate cre1 cDNA of strain Rut-C30.

Sequence analysis of the Rut-C30 cDNA clones showed that the 5' end of cre1 was identical to the previously sequenced cre1 of T. reesei up to nucleotide 261, corresponding to the first cysteine, $Cys_{87}$, of the second zinc finger (see FIG. 1), whereafter the two sequences differed. The reading frame of the truncated cre1 (hereafter referred to as cre1-1) continues after $Cys_{87}$, encoding eight additional amino acids (TSITCFFF) followed by a stop codon. A representative plasmid containing a 1.3 kb cre1-1 cDNA insert was designated pMI-42, and was deposited to Deutsche Sammlung von Mikro-organismen und Zellkulturen, Braunschweig, Germany, with DSM-accession number 10190, and was also stored in the VTT Culture Collection, Espoo, Finland with accession number VTT-F-95055. The DNA sequence of cre1-1 is given in SEQ. ID. NO. 6. The cre1-1 mRNAs are short and appear as a double band (1.1 and 1.3 kb) in Northern analysis (see FIG. 4). This is due to addition of the poly-A tail at two different regions as demonstrated by sequencing of four cDNA clones. The 3' end of the cre1-1 is dissimilar to all known Trichoderma gene sequences.

Figure 4:
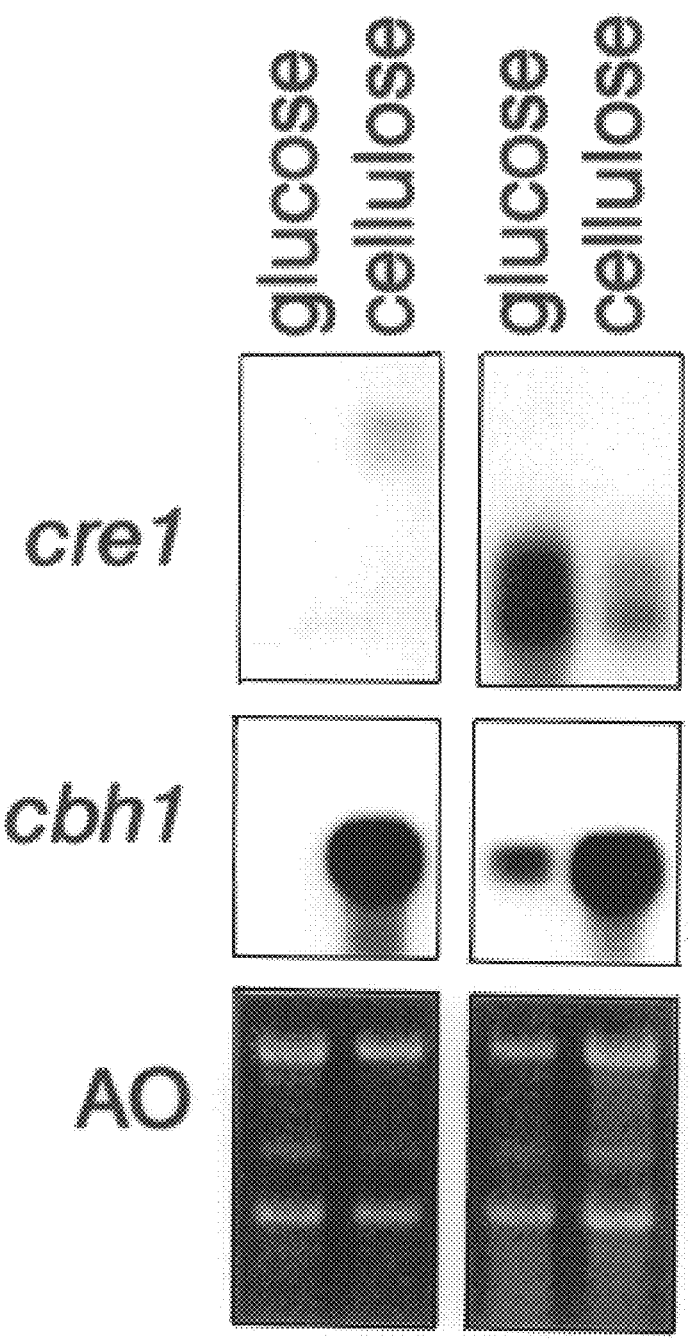
FIG. 4 Comparison of expression of cre1 and cbh1 in the *T. reesei* strains Rut-C30 and QM9414 cultivated for 72 h on 5% glucose or 2% solca floc cellulose medium. Northern analysis was performed as described in the legend to FIG. 2. The cre1 probe used was the 294 bp long fragment specific for the nucleotides from −158−+136 of the cre1 gene.

To study expression of the truncated form of cre1 and to compare that with expression of cre1 of strain QM9414, Northern analysis was carried out using a probe specific for the 5'-end sequences of the cre1 transcripts present in both the wild type cre1 and the cre1-1 of Rut-C30 thus establishing similar hybridization conditions. cre1-1 mRNA of Rut-C30 seems to be more abundant than the cre1 mRNA of strain QM9414, especially on glucose medium where the expression level of cre1-1 is markedly elevated (FIG. 4).

The Rut-C30 strain was originally isolated as a hypercellulolytic strain by screening for carbon catabolite derepression (Montenecourt and Eveleigh 1979) and it is consequently of interest to study the extent of possible glucose derepression of cellulase expression in this strain. The T. reesei strains Rut-C30 and QM9414 were cultivated on glucose and in inducing conditions on Solka floc cellulose. Expression of the major cellulase, cellobiohydrolase I (cbh1), was studied (FIG. 4, middle panel). cbh1 mRNA was produced by both of the strains on cellulose containing medium as expected. On glucose medium expression of cbh1 was repressed in QM9414 as shown previously (Penttilä et al. 1993), whereas Rut-C30 produced relatively high levels of cbh1 mRNA indicative of glucose derepression.

EXAMPLE 5

Transformation of the Mutated Gene cre1-1 of Rut-C30 into the Strain QM9414 to Replace cre1 with cre1-1

The endogenous cre1 gene of Trichoderma reesei QM9414 was replaced by the mutated gene cre1-1 of Rut-C30. For this purpose an expression vector pMI-62 was constructed (FIG. 5) in the plasmid pBluescript SK⁻ consisting of 5'-sequences of cre1 joined in frame to the cre1-1 cDNA followed by the amds gene and cre1 terminator. This construct was transformed to the strain QM9414 and transformants were selected based on utilization of acetamide as the sole nitrogen source. Transformant DNA were analysed by Southern hybridization to find those in which homologous recombination had taken place and the endogenous cre1 locus was replaced by the transformed construct. The transformant is viable and grows well, the growth rate being dependant on the growth medium used. Furthermore, the transformant produces cellulases in the presence of glucose in the medium.

In this way it was possible to construct a strain expressing the mutated gene cre1-1 and transfer the glucose derepressed phenotype of Rut-C30 into another Trichoderma strain.

EXAMPLE 6

Transformation of the Trichoderma reesei Strain Rut-C30 with Full Length cre1 Gene The cosmid clone pCOS11 carrying the cre1 gene was isolated from a cosmid gene library of chromosomal T. reesei DNA of the strain VTT-D-80133. From a positive clone (pCOS11) a 6.4 kb SalI-HindIII restriction fragment containing the protein coding region with flanking regions of cre1 gene was isolated and cloned to a SalI-HindIII cut vector pSP73 resulting in plasmid pMI-41. pMI-41 with plasmid p3SR2 (Hynes et al., 1983), that carries acetamidase gene as a selection marker providing the transformants the ability to use acetamide as a sole nitrogen source, were co-transformed to the strain Rut-C30 according to Penttilä et al. 1987. The integration of cre1 gene in the genome of acetamide utilizing transformants was verified by dot blot hybridization of chromosomal DNA to the 600 bp long cre1 probe lacking sequences found in the endogenous mutant cre1-1 in Rut-C30.

Figure 6:
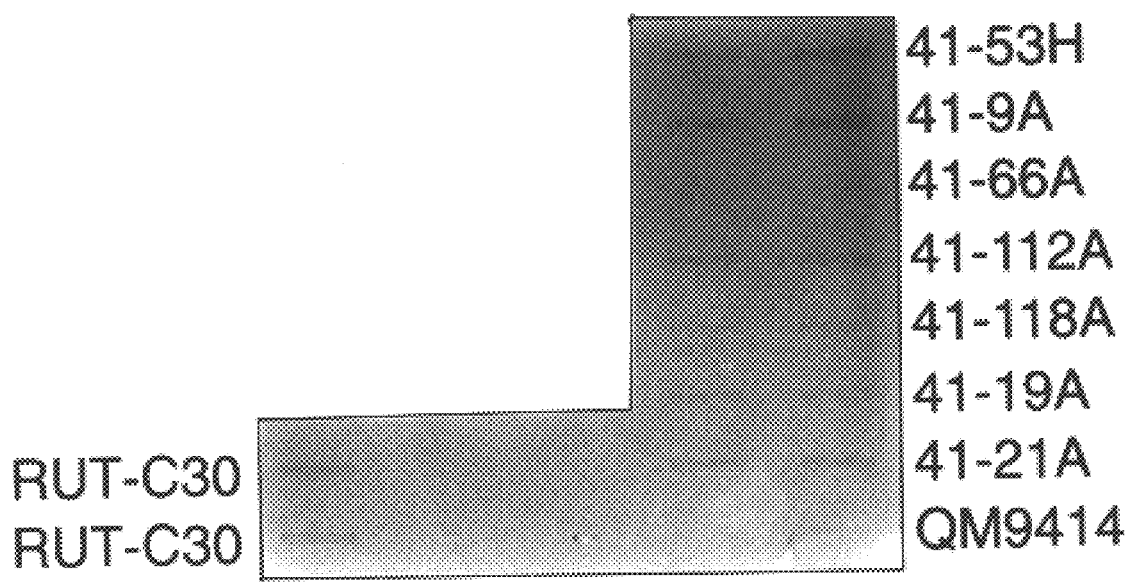
FIG. 6 Production of CBHI into the culture medium by *Trichoderma reesei* transformants. 40 µl and 200 µl aliquots of culture medium were dot blotted onto a nitrocellulose membrane after 3 days of cultivation in Trichoderma minimal medium containing initially 5% glucose and 0.2% proteose peptone. Monoclonal antibody CI-258 raised against CBHI was used to detect CBHI. Transformants 41-53A and 41-112A, 41-108A, 41-19A and 41-21A are AmdS$^+$ and cre1$^+$, 41-53A and 41-9A are AmdS$^+$. The host strain Rut-C30 and the strain QM9414 are shown as controls.

To study production of cellulases in cre1 transformant colonies, the host strain Rut-C30 and the strain QM9414 were cultivated in microtiter plate wells in minimal medium containing 5% glucose for 3 days. At this point of cultivation glucose was still detectable in the medium (in repressing amounts). Culture medium was dot blotted onto nitrocellulose membrane. Cellulases produced into the medium were detected immunologically using antibodies (FIG. 6). Monoclonal antibody CI-258 raised against the major cellulase CBHI was used (Aho et al., 1991). The analysis showed that the strain QM9414 did not produce any detectable CBHI, indicative of glucose repression of cellulase expression, but Rut-C30 and the cre1 transformants did, indicative of derepression. This shows that the mutated gene cre1-1 of Rut-C30 has a function that dominates (or codominates) in the transformants over the transformed cre1, or an additional mutation in Rut-C30 is partly taking part in glucose derepression in addition to cre1.

6.1 Effect of Transformed cre1 on Colony Growth on Solid Media

Spores of cre1 transformants and for comparison of transformants harbouring only the selection marker were plated on solid media to obtain colonies derived from a single spore. The medium used was potato dextrose agar (Difco) supplemented with 0.1% Triton X-100 to restrict spreading of the colonies. After 4–5 days of incubation at 28° C. a difference in growth was seen between cre1 transformants and the ones having only the selection marker, cre1 transformants formed bigger colonies than the others indicative of positive effect of cre1 on the growth/viability of the fungus.

Figure 7:
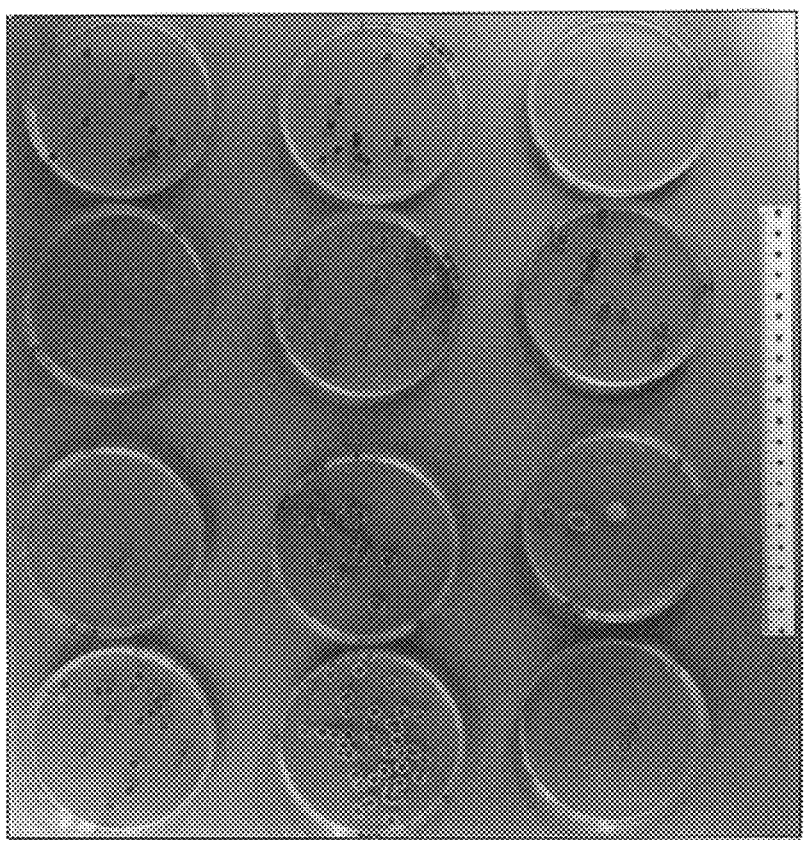
FIG. 7 Trichoderma strains Rut-C30 (left), Rut-C30 transformed with pMI-41 (middle), and QM9414 grown on Trichoderma minimal plates supplemented with 2% glycerol (top row), 2% glycerol +0.2% peptone (2nd row), 2% glucose+0.2% peptone (3rd row), and 2% glucose (bottom row).

When transformant colonies were cultivated on solid Trichoderma minimal medium containing 0.2% peptone supplemented with different carbon sources such as 2% glucose, 2% glycerol or 2% Solka floc cellulose and 0.1% Triton X-100, a difference in the colony morphology and diameter were seen between the host strain and the cre1 transformants in each case, the transformants being bigger (FIG. 7). For comparison, when peptone was omitted from the medium, no notable differences between transformants and the host strain were seen. In addition in the colonies grown on potato dextrose agar medium (Difco), the difference in colony growth was also seen. We conclude that cre1 affects the growth of the colony in a manner that is dependent on cultivation conditions especially on the presence of an organic nitrogen source.

6.2 Effect of Transformed cre1 on cbh1 Expression in Rut-C30

Figure 8:
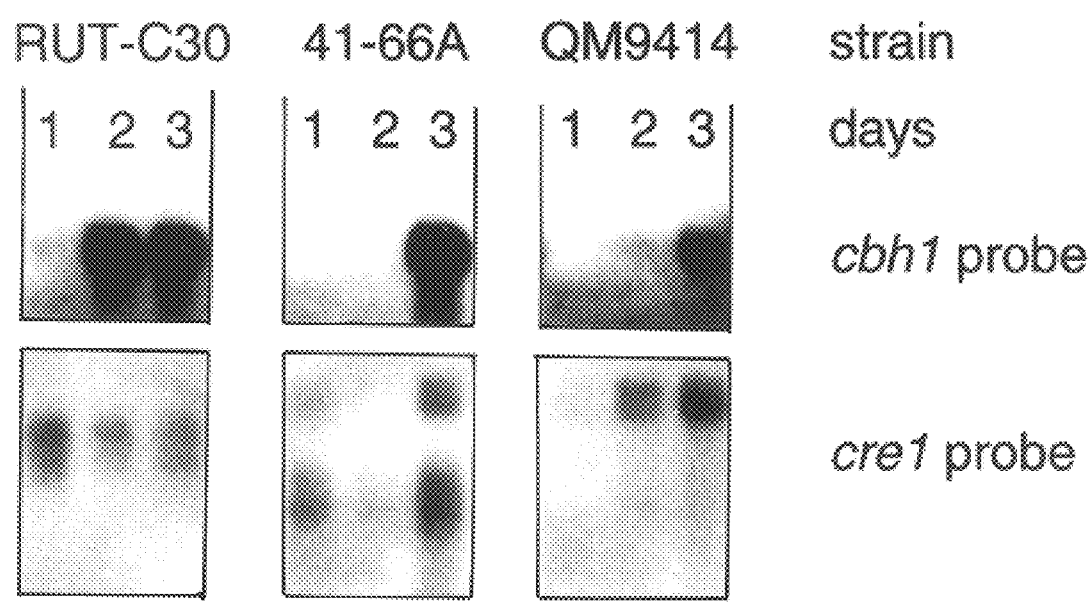
FIG. 8 Northern analysis on expression of cbh1 and cre1 mRNA by cre1 transformant 41-66A during cultivation in Trichoderma minimal medium containing initially 2% glucose and 0.2% proteose peptone. Total RNA was isolated from mycelia grown for 1, 2 and 3 days and 2 µg of total RNA was loaded on gel. The host strain Rut-C30 and the strain QM9414 are shown as controls.

Transformant colonies pMI-41-66A and pMI-41-112A and the host strain Rut-C30 were cultivated in liquid Trichoderma minimal medium containing initially glucose 20 g/l and 0.2% proteose peptone (Difco). After 1, 2 and 3 days of cultivation, mycelia were collected and total RNA was isolated. Northern analysis of cbh1 mRNA coding for the major cellulase cellobiohydrolase I (CBHI) showed that the strain Rut-C30 produced abundant cbh1 mRNA whereas in the transformants hybridization to cbh1 probe was significantly reduced (FIG. 8). Northern analysis of the same samples with cre1 probe showed that the transformed cre1 gene was expressed in the transformants. We conclude that the transformed cre1 was able to regulate cbh1 expression in the host strain.

6.3. Effect of Transformed cre1 on the Utilization of Glucose from Cultivation Medium Rut-C30 was transformed with pMI-41 containing the cre1 gene as described earlier. Two independent transformant colonies pMI-41-66A and pMI-41-112A were cultivated in Trichoderma minimal medium containing initially glucose 20 g/l as the sole carbon source and ammonium sulphate as the only nitrogen source in parallel with Rut-C30, the host strain for transformation in a rotary shaker at 28° C. for six days. Four parallel shake flasks for each strain were inoculated. The amount of glucose in the medium was monitored daily using the GOD-Perid method (Boehringer Mannheim) (Table 1).

The amount of glucose in growth media of the untransformed Rut-C30 decreased from the initial 20 g/l to 3–4 g/l during the first 3 days of cultivation and remained at that level till day 6. The amount of glucose in the cultivation medium of cre1 transformants decreased below the level that was detected in the growth media of the strain Rut-C30 when measured at day 4 and day 6, in some flasks no glucose was detectable. In addition in the culture medium of the strain QM9414 cultivated in parallel, glucose was no more detectable at day 6.

Based on these results we conclude that cre1 gene promotes consumption of glucose from culture medium especially when low level of glucose, below 3 g/l, is present.

TABLE 1

Amount of glucose (g/l) in growth medium. Cultivation was carried out in 250 ml conical shake flasks in 50 ml at 28° C. in a rotary shaker 180 rpm for 6 days. Cultivation medium was Trichoderma minimal medium containing initially 2% glucose.

|         | 2 d   | 3 d   | 4 d  | 6 d  |
|---------|-------|-------|------|------|
| RutC-30 | 14–16 | 3–4   | 3–4  | 2–4  |
| 41-66A  | 13–16 | 5–7   | 0–2  | 0–1  |
| 41-112A | 13–17 | 5–6   | 0–1  | 0–1  |
| QM9414  | 16–18 | 10–14 | 0–2  | 0    |

Deposition of Microorganisms

The following plasmid was deposited according to the Budapest Treaty to the DSM-depository (Deutsche Sammlung von Milkroorganismen und Zellkulturen GmbH, Mascheroder Weg 1b, D-38124 Braunschweig, Germany)

| Strain | Deposit number | Deposition date |
|--------|---------------|-----------------|
| Plasmid pMI-42 with the cre1-1 cDNA insert (in *E. coli* strain JA221) | DSM 10190 | Aug., 25 1995 |

REFERENCES

Aho, S., Olkkonen, V., Jalava, T., Paloheimo, M., Bühler, R., Niku-Paavola, M-L., Bamford, D., and Korhola, M. (1991) Monoclonal antibodies against core and cellulose binding domains of *Trichoderma reesei* cellobiohydrolases I and II and endoglucanase I. Eur. J. Biochem. 200: 643–649

Arst, H. N., and Bailey, C. R. (1977) The regulation of carbon metabolism in *Aspergillus nidulans*. In *Genetics and physiology of Aspergillus nidulans*. Smith, J. E., and Pateman, J. A. (eds). London: Academic Press, pp. 131–146.

Arst, H. N. Jr., Tollervey, D., Dowzer, C. E. A., and Kelly, J. M. (1990) An inversion truncating the cre4 gene of *Aspergillus nidulans* results in carbon catabolite derepression. *Mol Microbiol* 4: 851–854

Bailey, M. J., and Nevalainen K. M. H. (1981) Induction, isolation and testing of stable *Trichoderma reesei* mutants with improved production of solubilizing cellulase. *Enzyme Microb Technol* 3: 153–157.

Chirgwin, J. M., Przybyla, A. E., MacDonald, R. J., and Rutter, W. J. (1979). Isolation of biologically active ribonucleic acid from sources rich in ribonuclease. *Biochemistry* 18: 5294–5299

Dowzer, C. E. A. and Kelly, J. M. (1991) Analysis of the creA gene, a regulator of carbon catabolite repression in *Aspergillus nidulans*. *Mol Cell Biol* 9: 5701–5709.

Drysdale, M. R., Kolze. S. E., and Kelly, J. M. 1993. The *Aspergillus niger* carbon catabolite repressor encoding gene, creA. *Gene* 130: 241–245.

Hynes, M. J., Corrick, C. M., and King, J. A. (1983) Isolation of genomic clones containing the amdS gene of *Aspergillus nidulans* and their use in the analysis of structural and regulatory mutations. *Mol Cell Biol* 3: 1430–1439.

Mandels, M., Weber, J., and Parizek, R. (1971) Enhanced cellulase production by a mutant of *Trichoderma viride*. *Appl Microbiol* 21: 152–154

Maniatis, T., Fritsch, E. F., and Sambrook, J. (1982) *Molecular Cloning. A Laboratory Manual*. Cold Spring Harbor, New York: Cold Spring Harbor Laboratory Press.

Mathieu, M., and Felenbok, B. (1994) The *Aspergillus nidulans* CREA protein mediates glucose repression of the ethanol regulon at various levels through competition with the ALCR-specific transactivator *EMBO J* 13: 4022–4027

Montenecourt, B. S., and Eveleigh, D. E. (1977) Preparation of mutants of *Trichoderma reesei* with enhanced cellulase production. *Appl Environ Microbiol* 34: 777–782.

Montenecourt, B. S., and Eveleigh, D. E. (1979) Selective screening methods for the isolation of high yielding cellulase mutants of *Trichoderma reesei*. In *Hydrolysis of cellulose: mechanisms of enzymatic and acid catalysis.* Brown, R. D. Jr., and Jurasec, L. (eds). *Adv Chem Ser* 181: 289–301.

Mäntylä, A. L., Rossi, K. H., Vanhanen, S. A., Penttilä, M. E., Suominen, P. L. and Nevalainen, K. M. H. (1992) Electrophoretic karyotyping of wild-type and mutant *Trichoderma longibrachiatum* (*reesei*) strains. *Curr Genet* 2: 471–477.

Nakari, T., Alatalo, E. and Penttilä, M. (1993) Isolation of *Trichoderma reesei* genes highly expressed on glucose-containing media: characterization of the tef1 gene encoding translation elongation factor 1α. *Gene* 136: 313–318.

Nehlin, J. O., and Ronne, H. (1990) Yeast MIG1 repressor is related to the mammalian early growth response and Wilms' tumour finger proteins. *EMBO J* 9: 2891–2898.

Nevalainen, H., and Penttilä, M. (1995) Molecular biology of cellulolytic fungi. A review. In *The Mycota, vol II "Genetics and Biotechnology"*. Kück, U. (ed). Berlin: Spriger-Verlag, pp. 303–319.

Penttilä. M., Nevalainen, H., Rättö, M., Salminen, E., and Knowles, J. K. C. (1987) A versatile transformation system for the cellulolytic filamentous fungus *Trichoderma reesei*. *Gene* 61: 155–164.

Penttilä, M. E., Andre, L., Lehtovaara, P., Knowles, J. K. C. (1988) Efficient secretion of two fungal cellobiohydrolases by *Saccharomyces cerevisiae*. *Gene* 63: 103–112.

Penttilä., M., Saloheimo, A., Ilmén, M., and Onnela, M-L. (1993) Regulation of the expression of Trichoderma cellulases at mRNA and promoter level. Proceedings of the second TTUCEL symposium on *Trichoderma reesei* cellulases and other hydrolases, Espoo, Finland. Suominen, P., and Reinikainen, T. (eds). Foundation for Biotechnical and Industrial Fermentation Research 8: 189–197.

Raeder, U., and Broda, P. (1985) Rapid preparation of DNA from filamentous fungi. *Lett Appl Microbiol* 1: 17–20.

Sakai, A., Shimizu, Y., Kondou, S., Chibazakura, T., and Hishinuma, F. (1990) Structure and molecular analysis of RGR1, a gene required for glucose repression of *Saccharomyces cerevisiae*. *Mol Cell Biol* 10: 4130–4138.

Sambrook, J., Fritsch, E. F., and Maniatis, T. (1989) *Molecular Cloning. A Laboratory Manual*. 2nd ed. New York: Cold Spring Harbor Laboratory Press.

Stålbrand, H., Saloheimo, A., Vehmaanperä, J., Henrissat, B., and Penttilä, M. (1995) Cloning and expression in yeast of *Trichoderma reesei* β-mannanase containing a cellulose binding domain. *Appl Env Microbiol* 61: 1090–1097

Trumbly, R. J. (1992) Glucose repression in the yeast *Saccharomyces cerevisiae*. *Mol Microbiol* 6: 15–21

Unkles, S. E. (1992) Gene organization in industrial filamentous fungi. In *Applied molecular genetics of filamentous fungi*. Kinghom J. R., and Turner G. (eds). Glasgow: Blackie Academic & Professional, pp. 28–53.

Vanhanen, S., Penttilä, M., Lehtovaara, P., and Knowles, J. (1989) Isolation and characterization of the 3-phosphoglycerate kinase gene (pgk) from the filamentous fungus *Trichoderma reesei*. *Curr Genet* 15: 181–186.

Wolffhechel, H. (1989) Fungal antagonists of *Pythium ultimum* isolated from a disease suppressive Sphagnum peat. *Växtskyddsnotiser* 53: 7–11.

What is claimed is:

1. An isolated nucleic acid fragment comprising a polynucleotide sequence of nucleotides 316 to 600 the sequence of set forth in SEQ ID NO:6 or a polynucleotide which hybridizes to the complement of said nucleotides under the following conditions:

50% formamide, 5×Denhardt's, 5×SSPE, 0.1% sodium dodecyl sulfate(SDS), 100 μg/ml herring sperm DNA, 1 μg/ml polyA DNA at 42° C., said nucleic acid fragment encodes a polypeptide which maintains viability of a fungal host and relieves glucose repression in a fungal host.

2. An isolated nucleic acid fragment comprising a polynucleotide sequence of nucleotides 481 to 573 of the sequence set forth in SEQ ID NO:6 or a polynucleotide which hybridizes to complement of said nucleotides under the following conditions:

50% formamide, 5×Denhardt's, 5×SSPE, 0.1% sodium dodecyl sulfate (SDS), 100 μg/ml herring sperm DNA, 1 μg/ml polyA DNA at 42° C., said nucleic acid fragment encodes a polypeptide which maintains viability of a fungal host and relieves glucose repression in a fungal host.

3. An isolated genomic DNA fragment encoding a polypeptide comprising an amino acid sequence set forth in SEQ ID NO:7 or a polynucleotide which hybridizes to the complement of said genomic DNA fragment under the following conditions:

50% formamide, 5×Denhardt's, 5×SSPE, 0.1% sodium dodecyl sulfate (SDS), 100 μg/ml herring sperm DNA, 1 μg/ml polyA DNA at 42° C., wherein said polypeptide maintains viability of a fungal host and relieves glucose repression in a fungal host.

4. An isolated genomic DNA fragment encoding a polypeptide comprising amino acid residues 56 to 86 the sequence set forth in SEQ ID NO:7 or a polynucleotide which hybridizes to the complement of said genomic DNA fragment under the following conditions:

50% formamide, 5×Denhardt's, 5×SSPE, 0.1% sodium dodecyl sulfate (SDS), 100 μg/ml herring sperm DNA, 1 μg/ml polyA DNA at 42° C., wherein said polypeptide maintains viability of a fungal host and relieves glucose repression in a fungal host.

5. An isolated fragment nucleic acid according to claim 1, which is deposited with Deutsche Sammlung von Mikroorganismen und Zellkulturen GmbH under deposit accession no: DSM 10190.

6. A vector comprising a nucleic acid fragment of claim 1 operably linked with a promoter sequence.

7. A vector comprising a nucleic acid fragment of claim 2 operably linked with a promoter sequence.

8. A host cell transformed or transfected with a vector of claim 6.

9. A host cell transformed or transfected with a vector of claim 7.

10. A process for producing a protein in a fungal host comprising: transforming or transfecting a vector into a suitable fungal host; culturing the transformed or transfected host in a suitable growth medium comprising glucose; expressing a protein within the transformed or transfected host; and recovering the produced protein, wherein said vector comprises a promoter sequence operably linked to an isolated nucleic acid fragment comprising a polynucleotide sequence of nucleotides 481 to 573 the sequence of set forth in SEQ ID NO:6 or a polynucleotide which hybridizes to the complement of said nucleotides under the following conditions:

50% formamide, 5×Denhardt's, 5×SSPE, 0.1% sodium dodecyl sulfate (SDS), 100 µg/ml herring sperm DNA, 1 µg/ml polyA DNA at 42° C., said nucleic acid fragment encodes a polypeptide which maintains viability of a fungal host and relieves glucose repression in a fungal host.

11. The process according to claim 10, wherein the growth rate of the fungal host is controlled by a nitrogen source in the medium.

12. A process for enhancing the production of a protein in a fungal host, comprising transforming or transfecting a vector into a suitable fungal host; culturing the transformed or transfected host in a suitable growth medium comprising glucose; enhancing expression of a protein within the transformed or transfected host; and recovering the produced protein, wherein said vector comprises a promoter sequence operably linked to an isolated nucleic acid fragment comprising a polynucleotide sequence of nucleotides 481 to 573 the sequence of set forth in SEQ ID NO:6 or a polynucleotide which hybridizes to the complement of said nucleotides under the following conditions: 50% formamide, 5×Denhardt's, 5×SSPE, 0.1% sodium dodecyl sulfate (SDS), 100 µg/ml herring sperm DNA, 1 µg/ml polyA DNA at 42° C., said nucleic acid fragment encodes a polypeptide which maintains viability of a fungal host and relieves glucose repression in a fungal host.

13. The process according to claim 12, wherein the protein is secreted.

14. The process according to claim 13, wherein the fungal host belongs to the genus Trichoderma.

15. A process for producing a protein in a fungal host comprising: transforming or transfecting a vector into a suitable fungal host; culturing the transformed or transfected host in a suitable growth medium comprising glucose; expressing a protein within the transformed or transfected host; and recovering the produced protein, wherein said vector comprises a promoter sequence operably linked to an isolated nucleic acid fragment comprising a polynucleotide sequence of nucleotides 316 to 600 the sequence of set forth in SEQ ID NO:6 or a polynucleotide which hybridizes to the complement of said nucleotides under the following conditions:

50% formamide, 5×Denhardt's, 5×SSPE, 0.1% sodium dodecyl sulfate (SDS), 100 µg/ml herring sperm DNA, 1 µg/ml polyA DNA at 42° C., said nucleic acid fragment encodes a polypeptide which maintains viability of a fungal host and relieves glucose repression in a fungal host.

16. The process according to claim 15, wherein the growth rate of the fungal host is controlled by a nitrogen source in the medium.

17. A process for enhancing the production of a protein in a fungal host, comprising transforming or transfecting a vector into a suitable fungal host; culturing the transformed or transfected host in a suitable growth medium comprising glucose; enhancing expression of a protein within the transformed or transfected host; and recovering the produced protein, wherein said vector comprises a promoter sequence operably linked to an isolated nucleic acid fragment comprising a polynucleotide sequence of nucleotides 316 to 600 of the sequence set forth in SEQ ID NO:6 or a polynucleotide which hybridizes to the complement of said nucleotides under the following conditions: 50% formamide, 5×Denhardt's, 5×SSPE, 0.1% sodium dodecyl sulfate (SDS), 100 µg/ml herring sperm DNA, 1 µg/ml polyA DNA at 42° C., said nucleic acid fragment encodes a polypeptide which maintains viability of a fungal host and relieves glucose repression in a fungal host.

18. The process according to claim 17, wherein the protein is secreted.

19. The process according to claim 17, wherein the fungal host belongs to the genus Trichoderma.

* * * * *